United States Patent [19]

Hudson et al.

[11] Patent Number: 5,585,275
[45] Date of Patent: Dec. 17, 1996

[54] PILOT APPARATUS FOR PEPTIDE SYNTHESIS AND SCREENING

[75] Inventors: Derek Hudson, San Anselmo; Charles R. Johnson, Berkeley; Lutz Giebel, Burlingame, all of Calif.

[73] Assignee: Arris Pharmaceutical Corporation, South San Francisco, Calif.

[21] Appl. No.: 79,741

[22] Filed: Jun. 18, 1993

Related U.S. Application Data

[63] Continuation-in-part of Ser. No. 939,065, Sep. 2, 1992.
[51] Int. Cl.⁶ .................. G01N 33/543; C07K 17/00
[52] U.S. Cl. .................. 436/518; 436/523; 436/524; 436/527; 436/528; 436/529; 436/531; 530/333; 530/334; 422/68.1; 422/99; 422/129
[58] Field of Search .................. 436/518, 523, 436/524, 527, 528, 529, 531, 707; 530/333, 334; 422/68.1, 99, 101, 129, 131

[56] References Cited

U.S. PATENT DOCUMENTS

| | | | |
|---|---|---|---|
| 4,631,211 | 12/1986 | Houghten | 428/35.5 |
| 4,777,021 | 10/1988 | Wertz et al. | 422/101 |
| 4,965,087 | 10/1990 | Wolfbeis et al. | 427/2.11 |
| 5,010,175 | 4/1991 | Rutter et al. | 530/334 |
| 5,100,626 | 3/1992 | Levin | 422/100 |
| 5,188,733 | 2/1993 | Wang et al. | 210/321.84 |

FOREIGN PATENT DOCUMENTS

| | | |
|---|---|---|
| WO9015070 | 12/1990 | WIPO. |
| 91/13098 | 9/1991 | WIPO. |

OTHER PUBLICATIONS

Frank et al., "Facile and rapid 'spot–synthesis' of large numbers of peptides on membrane sheets", pp. 151–152 in *Peptides 1990*, ed. by Giralt et al., (1991) ESCOM Science Publishers B.V.

Schnorrenberg et al. Tetrahedron, 45, #24, pp. 7759–7764 (1989) "Fully Automatic Simultaneous Multiple Peptide Synthesis in Micromolar Scale–Rapid Synthesis of Series of Peptides for Screening in Biological Assays".

(List continued on next page.)

*Primary Examiner*—Lora M. Green
*Attorney, Agent, or Firm*—Oblon, Spivak, McClelland, Maier & Neustadt, P.C.

[57] ABSTRACT

Method and apparatus for simple and rapid preparation of reusable, addressable surface-immobilized arrays of biomolecules (libraries) used for screening for interaction with any biologically significant target. A special plate having on or in its surface a plurality of discreet functionalized substrate areas, typically in arrays of 10×10 to 400×400, is provided for chemical synthesis or bonding thereon of desired families of biomolecules (e.g. peptides, DNA, RNA, oligosaccharides). In the case of peptides, such as hexapeptides, the resulting permanently hexapeptide-loaded plate is a reusable Addressable Synthetic Peptide Combinatorial Library (ASPCL), in which 1 to 3 (typically two) of the positions in the sequence are uniquely identified by the address location. The preferred plate embodiment employs an HPMP wink of porous polyolefin removably received in holes in the plate. A unique multi-slot block assembly is used to prepare the ASPCLs. The wink carrier plate is also employed with a vacuum block system to assist in washing, deprotection, and probing. In library applications, for example determining peptides which bind to functional proteins (enzymes, receptors, antibodies), the substrate-bound peptides are assembled with several positions consisting of uniformly distributed equimolar mixtures of residues, and 2 separated or sequential positions uniquely identified by their spatial location on the substrate array, the "address". Following identification of the known residues giving the greatest affinity for the arrayed positions in the sequence, optimal binding for the complete peptide sequence is determined by an iterative process replacing formerly mixed positions with known AAs at unique addresses.

17 Claims, 5 Drawing Sheets

OTHER PUBLICATIONS

"Light–Directed, Spatially Addressable Parallel Chemical Synthesis" by Steph P. A. Fodor, J. Leighton Read, Michael C. Pirrung, Lubert Stryer, Amy Tsai and Dennis Solas, Research Article, Feb. 15, 1991, p. 767.

Generation and Use of Synthetic peptide Combinatorial Libraries for Basic Research and Drug Discovery by Richard A. Houghten, Clemencia Pinilla, Syl E. Blondelle, Jon R. Appel, Colette T. Dooley and Julio H. Cuervo, Nature, vol. 354, Nov. 7, 1992, p. 84.

Science and Technology—The Silver Shotguns, The Economist, Dec. 14, p. 119.

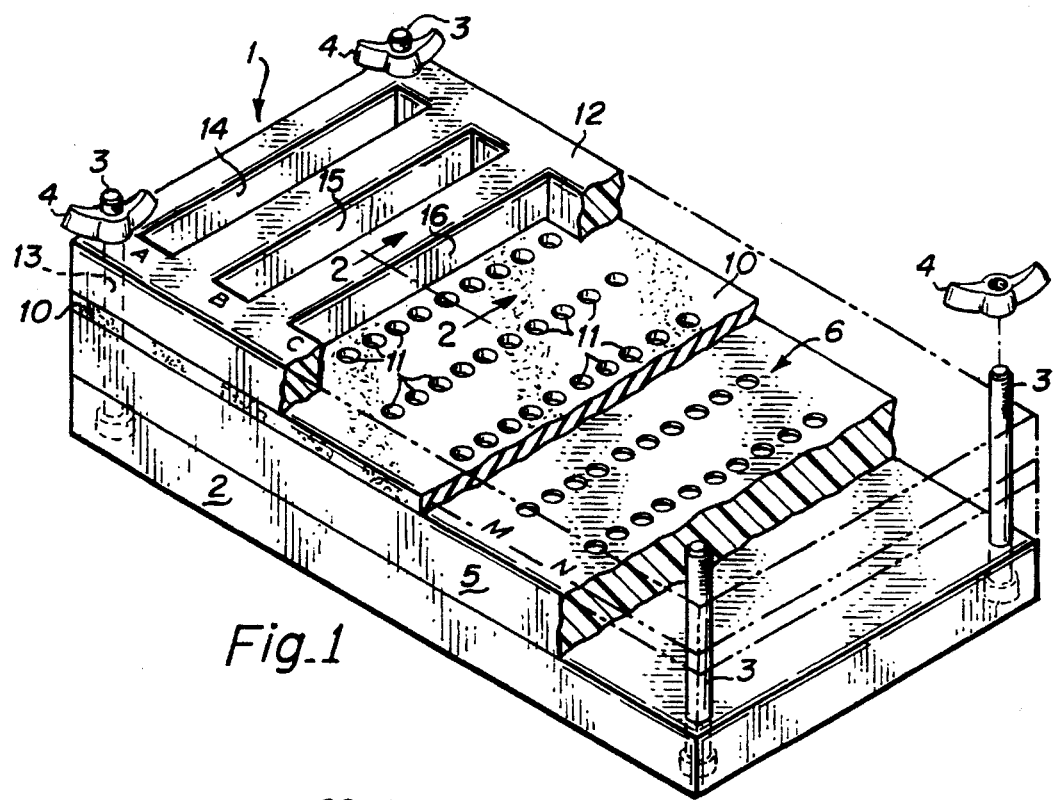
Fig_1
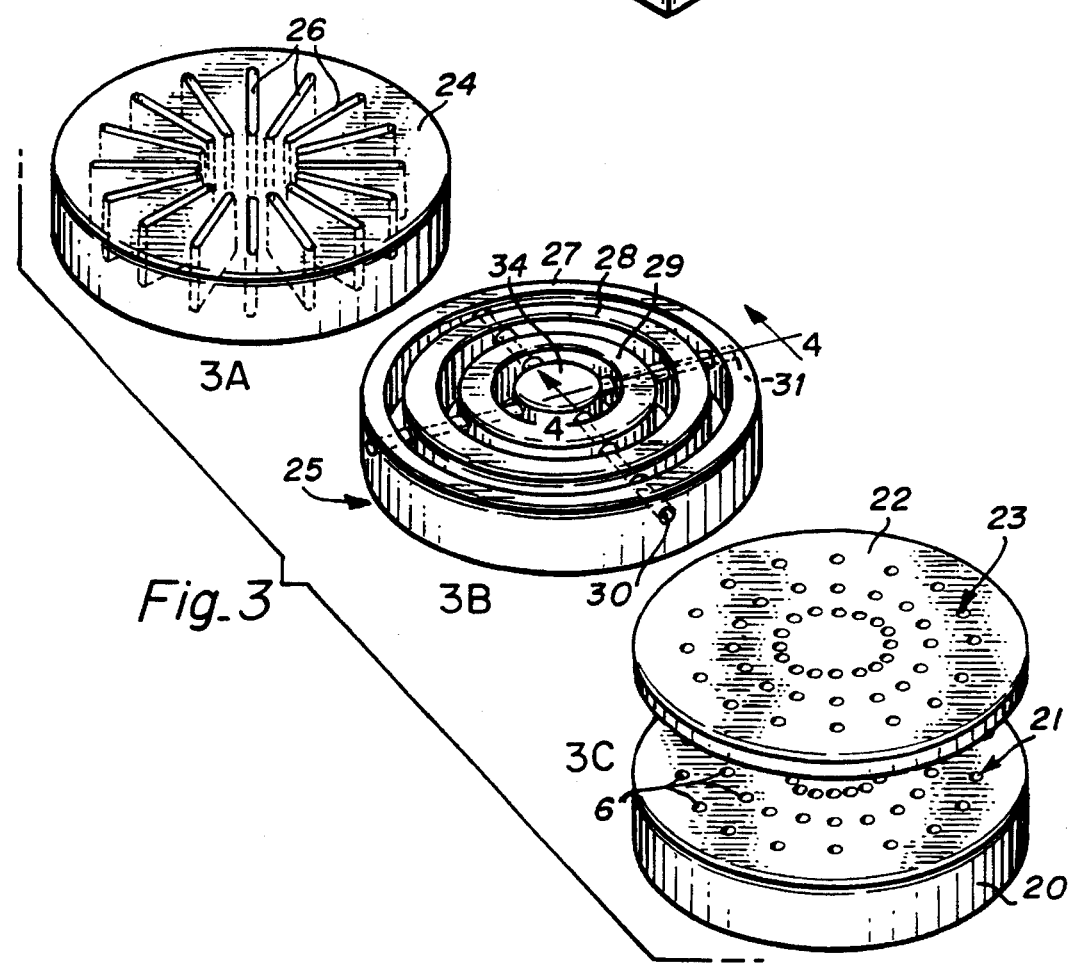
Fig_3

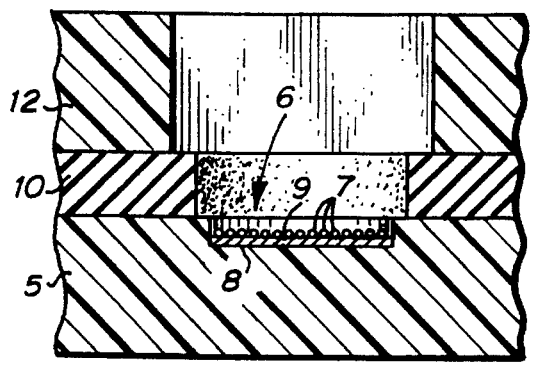
Fig_2a
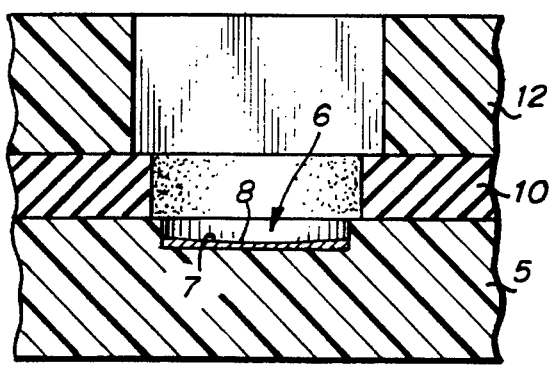
Fig_2b
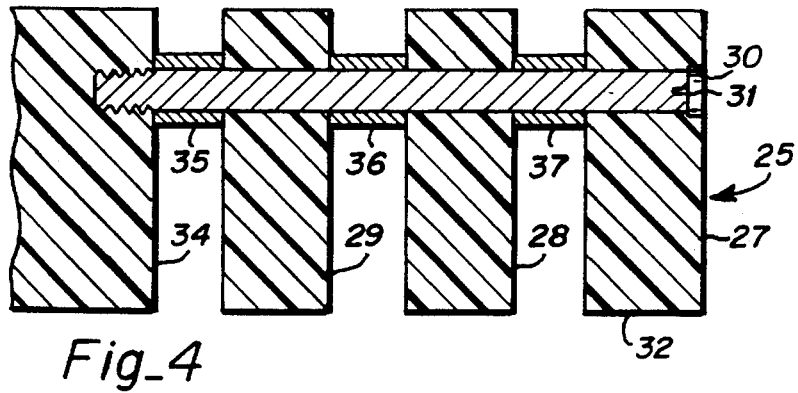
Fig_4
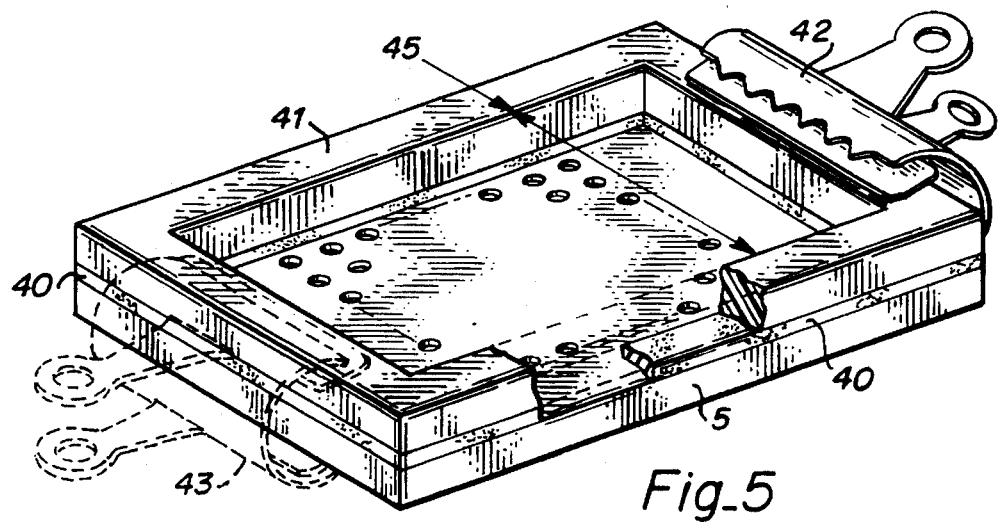
Fig_5

PILOT APPARATUS FOR PEPTIDE SYNTHESIS AND SCREENING

CROSS REFERENCE TO RELATED APPLICATIONS

This application is a continuation-in-part of our co-pending application Ser. No. 07/939,065 filed Sep. 2, 1992, of the same inventors entitled "Method and Apparatus for Peptide Synthesis and Screening." Our co-pending application Ser. No. 08/019,725 filed Feb. 19, 1993, "Thin Film HPMP Matrix Systems and Methods For Constructing and Displaying Ligands" discloses Hydrophilic Polar Multi-functionalized Polymers coated on porous sintered polyethethylene winks which may be used as removable substrate discs for the array plates of this invention. Conversely, the PILOT apparatus of this invention can be used in the library methods of our parent application Ser. No. 07/939,065, and in the methods of our related co-pending application 08/019, 725. The co-pending application Ser. No. 08/019,725 is hereby incorporated by reference herein.

FIELD

This invention relates to methods and apparatus for preparing a non-volatile, reusable, Addressable Synthetic Biopolymer Combinatorial Library (ASBCL) having known sequences at identifiable designated addresses arrayed on a permanent substrate, which library is rapidly creatable by a unique and simple slotted block system. The invention also relates to the use of ASBCLs to screen for sequences having biologic, biochemical, biomedical or therapeutic activity relative to a specified target. The invention permits rapid optimization of leads for identification of active components. When applied to the specific area of peptides. The invention may be termed PILOT, for Peptide Identification and Lead Optimization Technique.

BACKGROUND

Moderate length peptides have attracted considerable research and commercial interest by virtue of the properties some exhibit in enhancing, blocking or otherwise affecting the activity of receptors, microbes, and other molecules deemed biologically significant. Specifically, hexapeptides have proven to have a sufficient chain length to block much larger molecules such as receptors, enzymes and antibodies. Thus, synthetic and natural hexapeptides have exhibited diverse therapeutic properties, among them: Antimicrobials with minimum inhibitory concentrations an order of magnitude less than known natural antimicrobial peptides; bactericides; antivirals; activity as antigenic determinants; and the like. The problem is that there are 64 million (64 m) hexapeptide combinations for the twenty L-amino acids, and another 64 m for the D-amino acids. Indeed if the selection were made from all of the L and D combinations the number amounts to 4.096 billion. Since there are in turn millions of biologically/medically significant targets, preparing a complete suite of just 64 m L-hexapeptides and assaying activity for each of the millions of targets is, practically speaking, an infinite, and therefore, impossible, task.

Accordingly, the Synthetic Peptide Combinational Library (SPCL) approach has recently resulted in a manageable approach to the problem of screening for a unique hexapeptide among the 64 m that is the most active for a given target. In order to be feasible, libraries of large numbers of hexapeptides, on the order of 100,000 or so at a time, must be prepared in quantities sufficient to result in a positively determinable reaction.

There are currently five basic library techniques offered: viral approachs (originated by George Smith of LSU, and by Cetus and Affymax independently); the Chiron Geysen polyethylene pin system; the Houghten approach using Tea-bags; the Selectide bead approach; and the Affymax Chip approach. The latter four have distinct advantages over the viral approach in which peptide libraries are displayed by bacteriophages (viruses that prey on bacteria). A short degenerate oligonucleotide encoding all combinations of a short peptide sequence is cloned into Gene III or VIII of a filamentous phage and expressed on the phage surface. Recombinant phage are screened with the target molecule (e.g. receptor), and phage expressing a certain peptide that binds to the target are identified. Nucleotide sequence analysis of the recombinant Gene III or Gene XIII identifies the peptide sequence displayed by the binding phage.

The problem with the viral approach is that the range of peptides is limited to those tolerable by virus and *E. Coli*. That is, only a limited suite of peptides can be produced from among the 64 m possible hexapeptides, and likewise for the even greater numbers of longer peptides. Additionally, only L- amino acids are allowed, and each individual hexapeptide of the library is produced within the phage as fusion products. This reduces the flexibility of the sequences, and may mask them entirely.

Methods for synthesis and display of peptides on surfaces as well as techniques for binding from partial sequences were reviewed by H. Mario Geysen in Geysen, H. M. et al, Synthetic Peptides as Antigens, Wiley Chichester (Ciba Foundation 119), 130–149 (1986), shown in U.S. Pat. No. 4,833,092 (1989). Geysen used functionalized polyethylene pins clustered to fit 96 hole microtiter plates. This Chiron system also relies on the method shown in Rutter-Santi U.S. Pat. No. 5,010,175 of preparing peptide sequences by providing constituent amino acids in concentrations relative to each other based on their relative coupling constants so that the resulting peptide mixture contains peptides in equimolar amounts. Chiron reports that its recent U.S. Pat. No. 5,194, 392 entails synthesizing up to 1000 peptides a day on special pins, evidently a reference to the Geysen pin system of U.S. Pat. No. 4,833,092. The peptides can be used to "map" regions called epitopes in any protein of interest, such as antigen regions that trigger an immune response by T-cells.

The Selectide bead approach uses vast quantities of spherical crosslinked polymer beads (Millipore or Cambridge Research Laboratories polyacrylamide beads or Rapp Tentagel polystyrene) divided into 20 equal piles, each of which then has a different L-amino acid coupled to all the beads in the pile. The bead piles are then combined and thoroughly mixed. The resulting single pile is again divided into 20 different piles, each of which is reacted with a different one of the 20 different L-amino acids. This Divide, Couple and Recombine process (DCR) is repeated through six reactions to produce hexapeptides bound to the beads. The beads are then screened against a "target" molecule which is marked with a conjugated enzyme, such as horseradish peroxidase. The target "sticks" to active hexapeptide(s). The bead is rendered visible by adding a substrate for the enzyme which converts it to a colored dye which is precipitated within the beads, and then the visually identified bead(s) are picked out with tweezers. The peptides on the beads are then analyzed, for example by the Edman sequencing method, and soluble versions produced in a synthesizer. The initial screening (locating the target bead(s)) takes only days, the makeup of each identified hexapeptide is unknown, and the analysis and synthesis for confirmation and further work takes much longer.

The Houghten (Iterex) Tea-Bag method, shown in U.S. Pat. No. 4,631,211, employs methylbenzhydrylamine (MBHA) polystyrene beads in a number of foraminous containers, e.g. porous polypropylene bags (Tea-Bags), to prepare a truncated SPCL. In order to shorten the processing time, the Tea-Bag process employs partially known, partially undetermined hexapeptide sequences in repeated screenings, followed by iterative resynthesis to replace the unknown AA sequence positions with known AAs, i.e., $A-O_1O_2O_3XXX$, $A-O_1O_2O_3O_4XX$, etc. The method works on the assumption that a biologically significant response can be detected from a solution which contains hundreds of thousands of inactive components.

The Tea-Bag process typically uses 18 of the 20 L-AAs (cysteine and tryptophane are omitted in the initial library for ease of synthesis), starting with 104,976 combinations of non-determined tetrapeptide resins (XXXX-peptide resins) in 324 aliquots, and adds the 324 known dipeptide sequences ($18^2$) in the terminal two positions. For epitope determination of antibody binding, the 324 pools are screened to see which best inhibits binding of the target antibody with its natural antigen. The most active amino terminal dipeptide sequences are then incorporated into a further set of 20 pools in which the third residue is varied. These are rescreened for low IC. The most active sequences are again reincorporated iteratively to define positions 4–6 to finally obtain a characterized active hexapeptide.

The Tea-Bags employ MBHA-styrene beads and standard t-Boc chemistry (the conventional Merrifield method) in combination with simultaneous multiple peptide synthesis (SMPS) to prepare the starting $18^4$ non-determined XXXX-tetrapeptide library by a DCR process, which assures equimolarity of the peptides on the resin. Briefly, 18 porous polypropylene packets, each containing 4.65 mmol (5.00 g) of MBHA resin, are coupled with each of the protected N-x-t-Boc amino acids. Coupling reactions are checked to ensure they are complete (>99.5%) as assessed by Gisin's picric acid or Kaiser's tests. The resulting resins are then combined and thoroughly mixed as with the Selectide bead process. The resulting resin mixture is separated into 18 portions of equal weight which are placed into porous polypropylene packets, followed by N-a-t-Boc protecting group removal and neutralization of the resulting amine TFA salts. The resin packets are then reacted with solutions of the individual activated amino acids to yield the 324 dipeptide combinations ($18^2$). The above DCR process is repeated twice more, yielding a final mixture of 104,976 protected tetra-peptide resins ($18^4$). This XXXX-resin is divided into 324 aliquots (150 mg each) and placed in numbered porous polypropylene packets. Synthesis of the next two defined positions is carried out by SMPS. The peptide mixtures are deprotected and cleaved from their respective resins using low-high hydrogen fluoride (HF) in a multiple HF cleavage apparatus (Multiple Peptide Systems, San Diego, Calif.). Extraction of the individual peptide mixtures was carried out with $H_2O$. The competitive ELISA used is a modification of the direct ELISA technique, differing only in the antibody additions step in which 25 microliters each peptide mixture of the SPCL was added with a fixed dilution of the antibody (25 microliters per well).

The foraminous container of the Tea-Bag must retain the solid phase beads, yet have a sufficient number of openings to permit ready entrance and exit of solvent and solute molecules at the reaction temperature, but bar exit of the solid phase. While the synthesis is the standard Merrifield technique, new linking groups that attach the $X_n$-peptide to the styrene bead supports are disclosed. This process can be characterized as not calling for a continuous support, and it is not addressable.

The Affymax "chip" approach described in PCT publication WO90/10570, and in Fodor, P. A. et al, Science, 251 (1991) 767, is a method for multiple peptide synthesis on a solid support which uses synthesis and flourescent detection on the silica surfaces of flow through cells, photolabile protecting groups and photolithographic masking strategies to make arrays. Photolabilely-blocked amino groups are chemically attached (bonded) to a silicon chip, then irradiated through a patterned mask to selectively remove the blocking groups in a pre-arranged pattern. An amino acid will bond by addition only to the irradiation exposed areas. Additional masks are imposed and radiation applied as a prelude to adding second amino acids. Each amino acid added can include a blocking group so that further addition to that site occurs only after irradiation unblocking. Repeating the process with plural masks builds location specific polypeptides. When the chip is exposed to the target molecule, it may stick to one or more locations. By checking coordinates on a map of the chip, the peptide is identified. However, this process does not work with target molecules stuck to, or part of, cells, and there are exposure problems during processing, i.e., some AA's are light sensitive and cannot be used. Further, the reactions at the surface are not complete; for example, where reaction completion is only 90%, by the 6th iteration to obtain a hexapeptide, only half of them will be made properly.

Accordingly, there is a need in the art for a peptide synthesis and screening process that is rapid and accurately identifies the active peptides from amongst those in an extended, reusable SPCL.

THE INVENTION

OBJECTS

It is among the objects of this invention to provide methods and apparatus for creating a non-volatile, reusable Addressable Synthetic Biopolymer Combinatorial Library (ASBCL) having known amino acid sequences at identifiable designated addresses arrayed on a permanent substrate for rapid screening of target receptors and molecules.

It is another object of the methods and apparatus of this invention to produce ASBCLs in which the biopolymers are peptides, to provide ASPCLs for use in a Peptide Identification and Lead Optimization Technique (PILOT).

It is another object of this invention to provide an improved addressable substrate for adsorption thereon or bonding thereto of biopolymers, such as peptides in known AA sequences, by means of a slotted block system.

It is another object of this invention to provide a simple slotted block system which permits rapid multiple amino acid addition reactions to build peptides of known sequences at identifiable designated addresses in an X-Y coordinate array on a variety of planar substrates.

It is another object of the invention to provide a vacuum plate and base block system for retaining ultra-thin film-coated disc supports for rapid common synthesis steps and for probing of the arrayed molecules.

It is another object of this invention to employ sintered polyolefin discs as the substrates in the slotted block and vacuum plate assemblies of this invention for preparation of the general library arrays and probing methods of this invention.

It is another object of this invention to provide in combination a vacuum plate assembly for retainingly engaging sintered polyolefin discs having thereon ultra-thin HPMP films, more specifically carboxymethyl dextrans films that are carbodiimide coupled to the polyolefin disc surfaces functionalized with a diamino-substituted polyethylene glycol spacer arms.

It is another object of the invention to employ thin-film HPMP Winks in the plate and block assembly of this invention to permit display of assembled synthon molecules in an unhindered, near-aqueous environment, and thereby permit high quality peptide ligand synthesis, high ligand loading, efficient binding of radioactive target molecules and facile removal of unbound targets by suction washing, and repeated regeneration thereof.

Still other objects will be evident from the specification, drawings and claims of this application.

DRAWINGS

The invention is disclosed in more detail with reference to the drawings in which:

FIG. 1 is an isometric view of an assembled PILOT slotted block system apparatus, partly broken away to show the various parts in proper alignment and ready for introduction of AA's for reaction with the substrate areas or moieties thereon;

FIGS. 2a and 2b are section views taken in elevation along line 2—2 of FIG. 1 showing two alternative structures of a substrate area in detail;

FIG. 3 illustrates using a combination of two different blocks, one radial and one with concentric annular slots, with a circular support plate to produce a circular array;

FIG. 4 is a section view of the concentric annular block taken along line 4—4 of FIG. 3;

FIG. 5 is an isometric view of the peripheral frame system of this invention for functionalizing plates prior to condensing biopolymers thereon;

Figure 6:
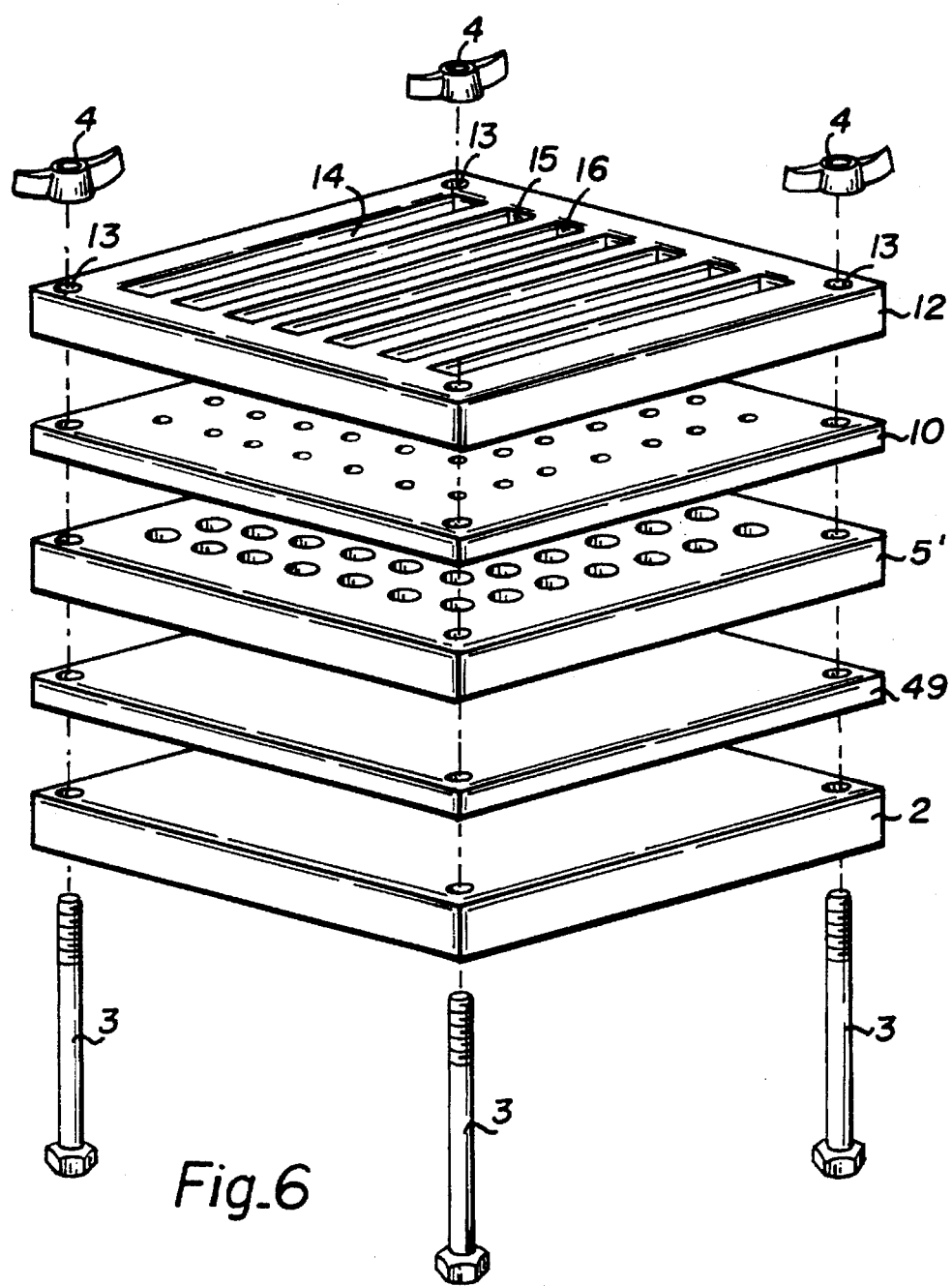
FIG. 6 shows in exploded isometric view the presently preferred embodiment of the slotted block assembly of FIG. 1 employing a vacuum disc-holding array plate for the array preparation steps.
Figure 9:
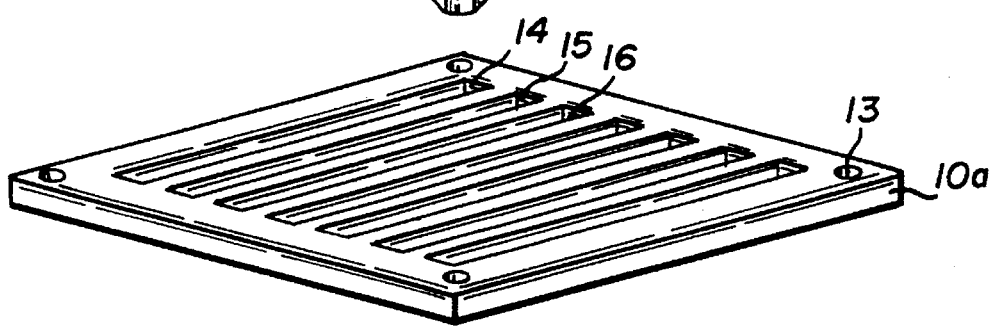
Figure 7:
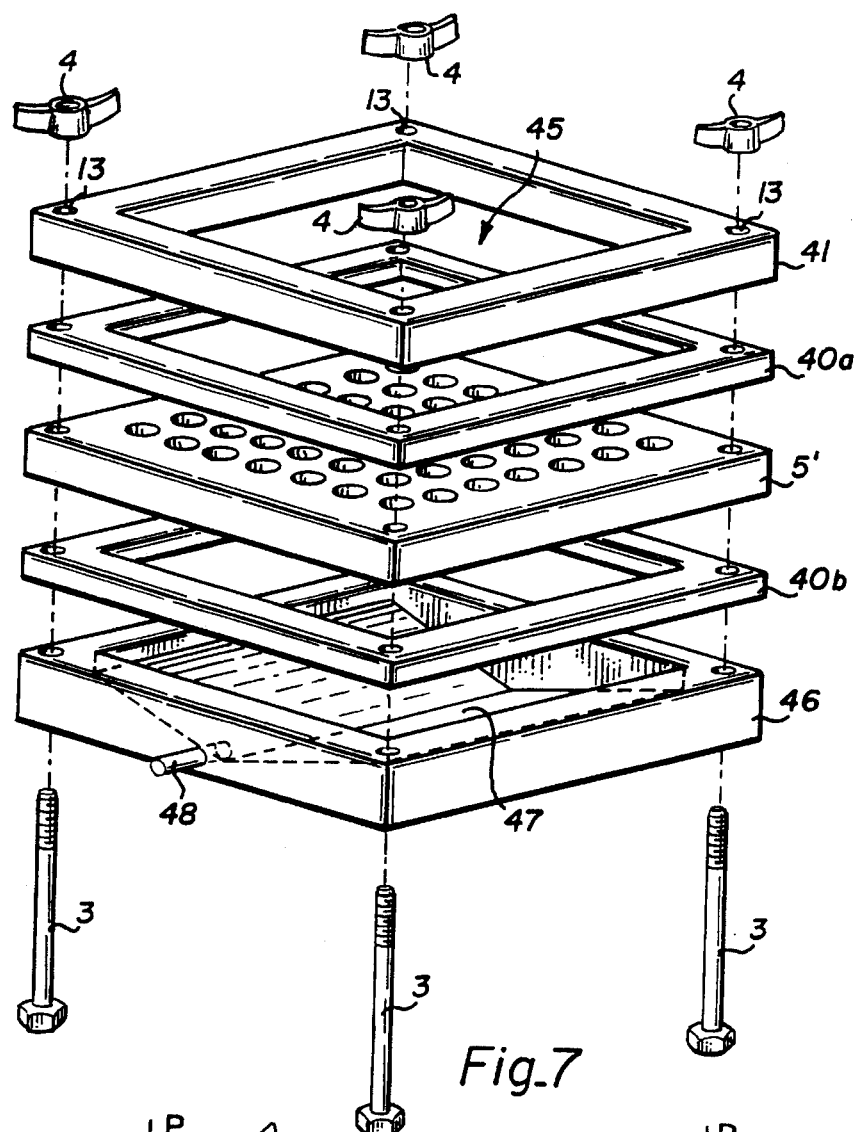
FIG. 7 shows in exploded isometric view the use of the vacuum plate on the vacuum base for common peptide synthesis and probing steps.
Figure 10:
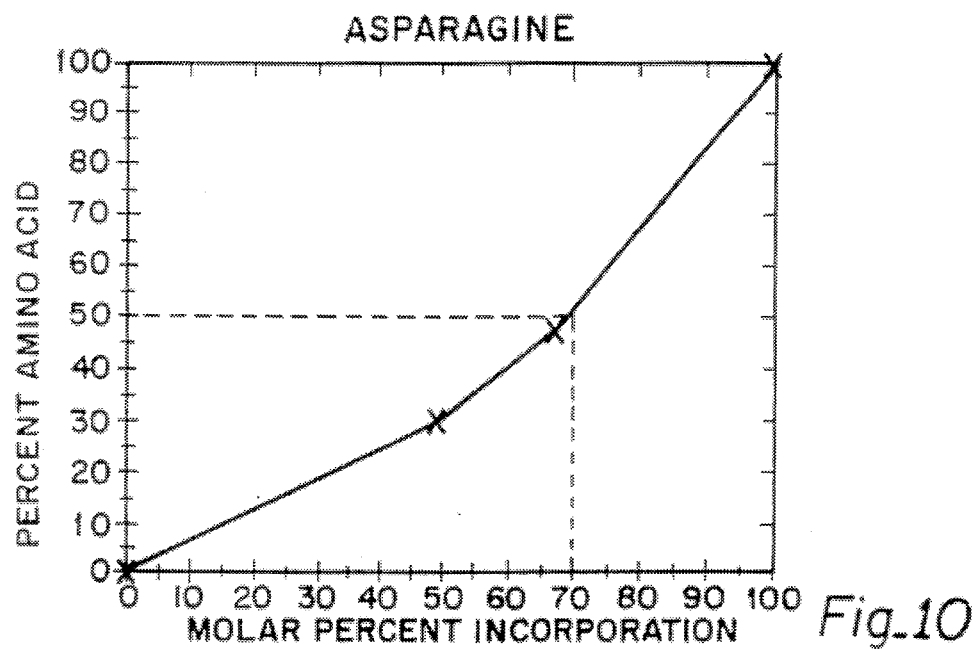
Figure 11:
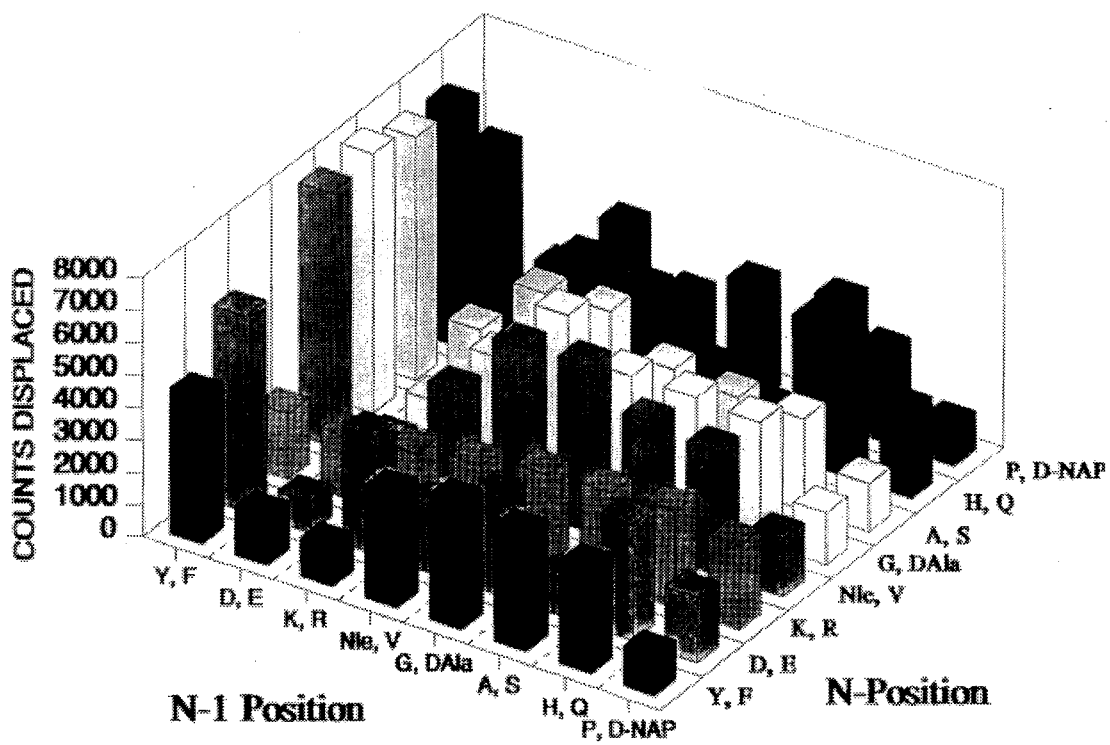

FIG. 9 shows in isometric a slotted gasket used above the plates of FIGS. 1, 6 and 7 in place of the multi-hole array gasket 10 of FIGS. 1 and 5;

FIG. 10 is a graph of the percent amino acid vs. molar percent incorporation in equi-molar mixtures to prepare the $\Omega$ mixtures used herein; and FIG. 11 shows the results of the $^{35}$S streptavidin array test.

SUMMARY

The invention comprises methods and apparatus for preparing non-volatile, reusable, Addressable SBCLs (ASB-CLs) or SPCLs (ASPCLs), having known arrayed dipeptide amino acid sequences incorporated at any desired and known position within any biopolymer (e.g., polypeptide) sequence of length producible by chemical synthesis methodology, in which up to 6 positions (typically 4) may be composed of mixtures of residues, the remaining positions comprising specified amino acids. The arrayed peptides are identifiable from designated addresses provided on a permanent, reusable substrate-containing plate which permits creation of an ASPCL, typically within a day. While the discussion herein is with reference to hexapeptides by way of example, the principles of the invention are applicable to any binding determinant biopolymer to produce an ASBCL for interaction with any biologically significant target. These library peptides are also termed ligands in our co-pending Ser. No. 08/019,725 filed Feb. 19, 1993, the disclosure of which is incorporated by reference herein.

The ASBCLs of this invention can uniquely identify the binding determinant biopolymer, e.g. an active hexapeptide, at a unique X-Y coordinate axis upon bonding with or adhering to a fluorescently labeled, radio-labeled or enzyme-linked target molecule or receptor, e.g., in solution flowed into contact with the ASPCL-bearing substrate. The amino acids and peptide sequences are substantially equimolar concentrations on the substrate, so good quantitative activity is determinable by the fluorescent or radio intensity, or by the optical density of the dye product formed in the enzyme linked probing.

In addition, the hexapeptide array is permanently bound to the substrate i.e., is non-volatile, and at each substrate site on the array plate on the order of 1µ mole or more can be bonded. The target molecule can be washed off the substrate plate so that it can be reused repeatedly, particularly for diagnostic testing, as well as rapid active peptide screening on a wide variety of target receptors. For example, a preselected library of peptides, or any other condensation chemistry-based screening agent, may be permanently bonded to a substrate as a diagnostic tool. One example involves exposing an ASPCL plate of this invention to one or more aliquots of a serum which requires diagnosis, and then visualizing binding by passing a flourescently or radio-labeled anti-IGG antibody over the ASPCL plate. Consequently, one or more conditions, such as the presence of antibodies to HIV-1, or the presence of other viral infections can be rapidly and simply diagnosed.

More broadly considered, the peptide may be any biopolymer. Thus the term ASBCL applies to the library on the identifiable designated addresses arrayed on the permanent, reusable substrate plate. It should be understood that the term "substrate" as used herein includes broadly but is not limited to: a) polyolefin plate alone, or, preferably, an activated plate carrying a plurality of substrate discs; b) a plate with a bead or gel substrate, amino functionalized or bare, (receptor substrate); c) such beads or gels with spacer arms, amino-functionalized or bare, (spacer receptor substrates); and d) reacted substrates i.e. such substrates above with one or more AAs or peptides linked thereto.

The apparatus system of this invention comprises employing an inert substrate support plate, such as a polyolefin polymer, having a plurality of discrete sites (such as holes for retainingly engaging removable substrate discs, called winks, or small, well-like, shallow flat-bottomed circular or square depressions) in a spaced array, e.g., 4×4, 10×10, 16×16, 20×20, 40×40, 100×100, 400×400, or any other desired number. The wink-holding plate array is presently preferred. Each of the sites are permanent uniquely addressable locations for assembly of the biopolyer chains or attachment of preactivated molecules. Each site includes an amino functionalized substrate media such as a sintered polyolefin (polyethylene or polypropylene) disc, glue-bonded beads, or chemically grafted polymeric films, which may be gel-type films. Any conventional peptide substrate, media, or addition chemistry-based agent substrate, may be used.

The preferred substrate is a ¼" diameter sintered polyethylene disc of approximately ⅛" thickness, which is coated with an ultra-thin Hydrophilic Polar Multi-functionalized Polymer (HPMP) film, herein called a "wink". The film and methods of anchoring to the polyolefin are disclosed in more detail in our co-pending application Ser. No. 08/019,725. The film is preferably carboxymethyl dextran carbodi-imide coupled to the polyolefin disc surfaces after functionalizing them with a diamino-substituted polyethylene glycol spacer arm. The films permit display of assembled synthon molecules (ligands) in an unhindered, near aqueous environment. These substrates permit high quality peptide (ligand) synthesis, high ligand loading in the film in the range of 50–100 nmole loading, efficient affinity binding of radioactive or flourescent labeled target molecules, and easy removal of unbound targets by suction washing, and repeated regeneration and reuse of the library. The substrate discs are easily pressed into and removed from holes bored partway through a substrate carrier plate, which preferably includes at least one smaller through-hole to permit rapid and thorough suction removal and washing of the array of substrate discs in the carrier plates. A vacuum base plate is used with the array carrier plate to facilitate the excess target solution removal and washing steps in the common synthesis and probing steps.

Examples of bead type substrates are polydimethylacrylamide (PDMA) particles, silica beads, MBHA polystyrene beads, and the like, which are glued to the substrate areas of the support plate. The presently preferred bead substrate is Kieselguhr-encapsulated PDMA particles (Pepsyn-K from Millipore Corp.), secured to a polyethylene plate with a low temperature (<100 degrees C) hot-melt polyethylene adhesive. The preferred polymeric film is chemically grafted to the surface of the wells by a process disclosed herein, and is particularly useful for screening involving large proteins.

Two methods of attachment of amino-functionalized polymers to form substrate areas on the plates are disclosed by way of examples of the principles of the invention; in situ polymerization (disclosed in detailed examples); and bonding of a pre-polymerized material to activated areas on the plate (disclosed in general). The first polymerizes acryloylated monomers and crosslinking agents onto acryloyl groups attached to the areas of the polyolefin surface (plate activation). This establishes a gel-type polymer covalently grafted into the depressions. This polymer, since it may possess low structural strength, i.e. it need not have high structural strength, can be prepared from monomers at low concentration and with a low molar percentage of crosslinking. The resulting gel substrate materials are therefore highly permeable to proteins, thus greatly improving the sensitivity of detection. The gel film may then be amino functionalized.

A spacer arm derivative is attached to the functional amino groups of the resultant films. These spacer arms, which are also used for the glued beads, increase sensitivity since they reduce unfavorable steric and electronic interactions between the incoming tagged protein and the polymer backbone. An ideal spacer is non-hydrophobic, incapable of forming aggregates by hydrogen bonding, and typically longer than 10 Å. A variety of materials, including functionalized polyethylene glycols, sugars, and short natural and unnatural peptides may be used as spacers.

The second (pre-polymerized) method of attachment of functional polymers involves attachment of preformed amino-functionalized polymers to the designated areas on the inert (polyolefin) support plate itself, or on the sintered polyolefin winks (discs) which are retained in the plate. The preformed polymer itself serves as a spacer arm, and access of proteins is improved as compared to the in situ gel type polymers. Examples of preformed amino-functionalized polymers include polyethyleneimine, polyallylamine, long chain functionalized sugars (e.g. dextrans), polyamino acids (e.g. poly-L-lysine) and the like. They can be coupled to acid chloride activated plate areas by reactions of the type described herein. We prefer to use a 500,000 MW dextran that is amino-functionalized pre- or post-attachment to the plate area, or to the winks as described in our co-pending Ser. No. 08/019,725.

For the array preparation steps an elastomeric sealing gasket having a plurality of holes or slots therethrough aligned with the substrate areas is placed over the substrate array plate or wink carrier plate, and a slotted block is placed over the gasketed plate so that individual slots align with rows of substrate areas. When the wink carrier plate is used, a solid non-apertured gasket is placed below the wink plate to seal the through-holes, and then placed on a base plate. The assembly of the plate, slotted block and appropriate gasket(s) is clamped together for use.

Since each area is part of a predetermined array, each defined substrate area has a unique X-Y coordinate address, such as: Row 1, position 1; Row 2, position 20; Row 3, position 78; to Row $X_n$, position $Y_m$. Any desired address system may be used, such as sequential numbers for each succeeding area, dual alpha system (AA, AB, AC etc.), or alpha numeric (A1, A2 ... B1, B2 ... ).

The slotted block has a height sufficient to provide a well of sufficient volume to receive reaction solution having selected moieties for bonding with the exposed substrate address area, or for reaction with a previous moiety. Each well can receive a different reactant, e.g. a blocked AA, so that each row has a different $A_n$ position AA. Next, the reactants are removed from the slots in the block, e.g. by decanting or suction, then the amino blocking group removed by a deblocking agent, e.g. piperidine. Then the slotted block (and slotted gasket if such is used) is rotated horizontally 90°, and each slot well receives another, same or different, reactant so that the $A_{n+1}$ position has a predetermined AA. Where the sequence of AAs are the same in each well at each block orientation, turning the block 90° produces all 400 combinations of dipeptides for a 20 slot block/400 substrate area plate system. Iterative application of 3 such plates, two positions being optimized at a time, allows for the identification of the single optimal binding peptide from a 64 m hexapeptide SPCL. The substrate areas can be quite small to provide peptides in adequate (picomolar) amounts, e.g., the ¼" diameter winks.

As an illustration of another method of use of the system of this invention, a random sequence of all XXXX-tetrapeptides on Pepsyn-K beads is prepared, and these beads adhered to the substrate areas. Alternately and preferably, a polymeric film gel (HPMP) may be prepared on a plurality of winks, which are then reacted in a flask (100 ml/100 winks) of an automated peptide synthesizer to produce the random XXXX-tetrapeptide mix. These winks are then pressed into the holes in a wink carrier plate. The wink plate is placed on a border or periphery gasket on a vacuum block, and then overlain with another border gasket and a "window frame" border block and clamped.

Then, using the system of this invention, the terminal two AAs can be added thereto in the all-combinations 20×20 array via the rotation of the slotted block assembly. Alternately, a known dipeptide can be added to the end terminal by two cycles of reaction with the vacuum block, say all VY, i.e., VY at all positions. A reaction cycle is defined as deblocking the prior reaction step AA, and reacting with the next blocked AA. The resulting hexapeptides are screened (probed) by exposure to labeled targets. This is done in the vacuum block assembly.

A deductive process involving iterative resynthesis of successively smaller libraries can be used to successively characterize the resulting screening-active hexapeptide. Alternately, the procedure and apparatus of this invention can work from a defined middle dipeptide with random ends, followed by replacement of each end in sequence with known dipeptides. Likewise 4 or 5 residues may be mixed, or an array of any kind of peptide, including those including one or more non-natural AAs, can be employed on the reusable substrate of this invention.

The use of winks receivingly engaged in the support address area is preferred for diagnostic or drug use applications, as single preselected, known-sequence peptide-containing winks can be prepared in place in the carrier plate, or separately prepared in an automated synthesizer and inserted in the holes in the support in specified address(es). Likewise, DNA moieties can be bonded to the support, in which case a 16×16 array, or an array of 16-4×4 subarrays, on a single plate is preferred.

Advantages of the apparatus and methods of this invention include: Synthesis of defined peptides, portions of which optionally can consist of redundant known or unknown (uncharacterized or non-defined sequence) mixtures which are bonded in micromolar amounts in defined arrays with known addresses so that a physical barrier (e.g. an appropriately apertured member) can permit simultaneous screening. Another feature is fluorescent or radiolabeled detection of binding, which provides higher sensitivity and is far more suitable for detection of low affinity interactions than the current Selectide or Iterex technology. The solid array support also permits inference of optional binding elements (e.g. AA sequences) from the spatial position (unique address) rather than requiring chemical determination of sequence.

The ASBCLs and ASPCLs constructed by the method and system of this invention are selectively variable at any two or more positions, while redundant (random selection of all combination) at several other positions (say, 3–6) within peptides or biopolymers of a wide range of size and structure. The system is also useful for screening (probing) by itself, or in conjunction with current methods (such as the Iterex Tea-Bag or Selectide methods), for any two or more AA position sequencing, and can be used for progressive refinement of initially identified hits (indications of activity).

Because of the effectiveness of the support system of this invention, the separate zones (one or more support address area(s)) can be functionalized for synthesis of peptides at loadings as low as about 0.001 micromoles per cm$^2$ usually in the range of from about 0.05 to about 50µ mole/area, and 50–100 nmole loading for HPMP winks.

The system also permits simultaneous or sequential synthesis by standard Fmoc or t-Boc-chemistry of identified areas (addresses) of distinct known or non-defined peptides, by attaching the slotted block to the substrate plate for simultaneously performing individual separate couplings in the slot compartments. By transforming the block orientation, arrays of peptides may be synthesized at any two positions within a peptide or biopolymer of any length. The previous or following AAs in the peptide sequence may be uniform across the entire substrate surface, and may be unique or consist of mixtures of one or more peptides of known or uncharacterized composition. Common steps can be carried out in the vacuum block system, and winks loaded with random peptides may be prepared in an automated peptide synthesizer.

While the same block is shown used in different orientations, e.g. rotating a slotted block 90°, two dissimilar blocks may be used in the array generating steps, such as a radial slot block (slots extending radially outwardly from a common center) in combination with a block with concentric circular (annular) slots, and the resultant array may be addressed by polar coordinates.

The system of the invention permits displacing the label on the target with a natural ligand to insure specificity of the identification. It also permits reuse of the substrate for repeated probing of the surface by alternative proteins i.e. exposure to different targets followed by washing. DMF washing is particularly easy by use of the vacuum block where the wash is removed by aspiration through the vacuum base. Different areas (addresses) may employ the same or different binding materials, e.g. Pepsyn K particles in one area, winks in another, and grafted films in another.

Although the method and apparatus shown herein are directed to definition of optimal binding linear hexapeptides, it has great applicability in different formats. Especially where the protein of interest, e.g. cytokine receptor, binds a large ligand, then it is advantageous to insert the library within longer sequences, particularly those which are known to form stable secondary structures, as in loops, beta conformations or alpha helices. In the latter, since the library is then displayed on a cylindrical surface, it is of interest to construct the components 3 or 4 residues apart, the components being separated by helix-forming residues, such as alanine. For libraries based on loop structures, either end may be designated as a Cys residue which can then be coupled together by intramolecual disulfide bridges. Cyclic peptides, especially cyclic hexapeptides and cyclic decapeptides can be constructed on PILOT substrate matrices of this invention, and are especially useful for the relative rigidity of these molecules compared to their linear counterparts. Also, bogus pseudo array checking can be easily done with the system of this invention.

The novel PILOT ASBCL's and methods of this invention provide distinct advantages over the numerous alternatives discussed above in the Background to meet the need for developing new pharmaceutically useful compounds. The specificity of the binding may be uniquely established by side-by-side comparative processing of dual plates which are then probed, one with the presence of the natural ligand, the other without, and the two compared.

One particular advantage of the invention is that it allows detection by numerous methods, but it is unique in being suitable for detection with radiolabelled derivatives, with autoradiographic and counting methods providing the enhanced sensitivity vital for the detection of relatively low-affinity binding peptides which are present in picomolar amounts within pools containing thousands of other non-binding sequences. Use of $^{125}$I labeling with Bolton-Hunter reagent provides sensitive and simple detection by auto radiography. With $^{35}$S and $^{14}$C labeling, arrays are recoverable and can be reprobed numerous times after scintillation counting of individual winks pushed out of the carrier (holding) plate.

Another advantage of the invention is that it allows for the use of standard substrate materials (e.g. HPMP winks or Pepsyn K for peptide synthesis, and HPMP winks or controlled pore glass for DNA/RNA synthesis), for synthesis on the plates, or for preassembly by automated synthesizers followed by arraying these for diagnostic applications. In library applications, the unique method of grafting in-situ generated polymers or attaching preformed polymers to functionalized polyolefin surfaces such as winks provides materials far better suited for screening methods than conventional particulate solids. A special virtue is the optical clarity of the HPMP film substrates of this invention, combined with their low intrinsic fluorescence which greatly enhances the sensitivity when used with fluorescent tags. Of even greater importance is that the substrate HPMP films of this invention are formulated to provide excellent penetration of proteins within their bounds, and side-by-side comparisons with prior art methods have shown significantly enhanced sensitivity with use of this invention. In particular, the invention allows the addition of covalently-modified long chain polysaccharides, such as carboxymethylcellulose (CMC) or dextran, to functionalized substrate surfaces. The substrate (SU) may be any bio-compatible, functionalizable or pre-functionalized material capable of covalent bonding to spacer arm anchor molecules. Examples of such substrates include solid substrates (monolithic blocks), membranes, films, laminates, spherical and irregular particles, and woven or non-woven filtration materials prepared, for example, from polyolefins, such as polyethylene, polypropylene, halogenated polyolefins (such as PVDF, PVC etc.); polystyrenes; polyacrylamides; copolymers of the above co-polymers with the other polymers; cellulosics (including cottons, and other natural and synthetic fibers), and inorganic materials (including alumina, ceramics, titanium oxides, silica, silicon, glass, and the like).

The surface of the support may be functionalized in a variety of ways to provide amino or carboxyl functionalization sites for bonding thereto of the spacer arm anchor molecules. For polyolefins, oxidation with chromic acid provides a rapid and simple procedure. Alternatively, other functionalization (e.g., via high pressure reaction with oxalyl chloride, plasma oxidation, or radical-induced addition of acrylic acid) may be provided. Halogenated materials (e.g., plastics) may be functionalized by base-catalyzed elimination processes introducing double bonds, followed by subsequent addition of amino-functionalized derivatives. Silicas, aluminas, titanium oxides, ceramics and silicons may be conveniently functionalized with any of a variety of commercially available substituted silanes (e.g., aminopropyltriethoxysilane). Hydroxylic compounds (cellulosic membranes, filters, cottons, etc.) are simple to derivatize via a variety of methods. They can be directly carboxymethylated (e.g., with bromoacetic acid); acylated directly with a protected amino acid (e.g., via dimethylaminopyridine catalyzed carbodi-imide coupling with tBoc-glycine). A particularly advantageous method is reaction with carbonyl diimidazole (or phosgene or triphosgene), followed by reaction with a diamine or monoprotected diamine to introduce amino functionalization via a highly stable urethane linkage.

The HPMP matrix material may be any biocompatible, substantially uncrosslinked, high molecular weight, highly soluble polysaccharide, $[S]_n$. Particularly useful are commercially available high molecular weight dextrans (e.g., Pharmacia Dextran T500), although a variety of other polysaccharides (e.g., carrageenans, and guaiac acid derivatives) are suitable alternatives. Carboxymethyl- or amino-functionalized polysaccharides such as cellulose are also suitable.

The degree of functionalization, expressed as functional groups (FGs) per saccharide unit, [S] ranges from about 1:1 $FG:[S]_x$, to about 1:100 $FG:[S]_x$, i.e., x ranges from 1 to 100 per functional group. The molecular weight, MW, of the HPMP polymer may range from about 10K (10,000) to about 10 MM (10 million), with an average around 2 MM, where the polymeric unit is a saccharide. For the typical polysaccharide HPMP of this invention $[S]_n$, n ranges from about 500 to 50K. As noted below, the HPMP strand is anchored in plural places to the substrate support surface, SU. In the anchored, folded or convoluted condition, the HPMP forms a thin film layer on the order of about 1000 Å thick (100 nm), where $[S]_1$=1 nm=10 Å. Of course, other polymers will have somewhat different lengths. The HPMP must have substantially no crosslinks in order to maintain the matrix flexible, open and freely permeable to the TTMs (tagged target molecules).

The attachment of the display matrix polymer strand to the substrate surface may be performed by a variety of procedures. It is important that the attachment chemistry functions efficiently in aqueous media to form highly stable chemical bonds. Single point attachment of an HPMP, such as a dextran, to amino-functionalized surfaces is obtained by reductive amination in the presence of sodium cyanoborohydride, of the reducing end of the sugar to an amino functionalized anchor. Alternately, there may be direct attachment to an amino-functionalized substrate surface. This method gives a low anchor density, i.e., number of anchors per cm² of substrate surface. We prefer methods which form a plurality of attachment points (e.g., 0.001% to 25% of available substrate surface functionalized sites) that are stable during synthesis of ligands and subsequent probings. Stable stapling is needed so that what little glycosidic bond hydrolysis that may occur between the HPMP and the spacer arm, happens only during the more drastic chemical treatments involved in subsequent synthesis of ligands (e.g., piperidine in DMF, trifluoroacetic acid+ethane dithiol+thioanisole) or during displacements of TTMs, so that little or none of a displayed ligand library will be lost.

The most preferred attachment of the HPMP to the substrate support involves functionalizing the surface with spacer arm anchor molecules and reacting them with the HPMP by amide bonds. This process is termed "stapling". If the substrate surface bears pendant functional carboxyl groups, e.g., terminal carboxyls on anchor molecules, these must be coupled to amino-functionalized HPMP's, e.g., aminated polysaccharides, by aminating the HPMP before ligand tethering. Both the stapling linkage and tether linkage functional groups can be provided simultaneously by aminating the HPMP with sufficient amino groups for both anchoring and for tethers for ligand attachment. Conversely, if the support surface bears pendant amino groups (on the surface itself or on terminals of anchors) then attachment is achieved by coupling to carboxyl functionalized HPMPs, e.g., carboxymethyl polysaccharides. Unreacted carboxyl groups are then reactivated and coupled to mono-protected bisamines to provide display sites for the ligands.

In another variation, both the masked amino and carboxyl functional groups are incorporated on the polysaccharide. Then, base treatment liberates carboxyl groups for attachment, directly or indirectly, to amino functionalized surfaces or ligands. Alternatively, acid treatment liberates amino groups on the HPMP for attachment to surfaces or ligands that are directly or indirectly carboxyl functionalized.

The chemistry used for polysaccharide-type HPMP coupling (stapling and tethering) is essentially the same, either preforming active ester derivatives with carbodiimide reagents, and then adding the amino component, or preforming activated species in the presence of both amino and carboxy-components.

Any particular attachment can be "tuned", that is the amount degree or density of anchors stapling the HPMP to the substrate support surface can be controlled, as well as the quantity, degree or level of functionalization of the surface. Thus it is possible to produce different proportions of polysaccharide to surface attachment points (stapling) compared to the loading (concentrating) ligand/library display sites.

The use of spacer arm anchor molecules is preferred over direct stapling of the HPMP to the substrate surface. The spacer arms facilitate stapling of the HPMP to the surface and, as noted above, permits control of anchor density (degree of stapling). A typical spacer arm molecule spaces the HPMP matrix layer from about 15 to about 50 Å from the substrate surface. A typical spacer may be any biocompatible bifunctionalizable molecule that permits quantitative control of attachment density to the substrate. Examples of alternative spacers include: $C_2$–$C_{30}$ α, ω diaminoalkanes, e.g. 1,3-diaminopropane and 1,6-diaminohexane; a variety of peptides (e.g., oligomers of beta-alanine, aminocaproic acid); polyglycol type derivatives (such as Jeffamine ED-600 from Texaco, O,O'-Bis (2-aminopropyl)-polyethylene glycol 500; and 2,2'-(ethylenedioxy)-diethylamine from Fluka). The presently preferred spacer is Jeffamine ED-600. A typical density is $10^{16}$ anchors/cm$^2$ surface area, but may range from about $10^9$ to about $10^{22}$ anchors/cm$^2$.

As noted, it is important that there be substantially no intra-HPMP crosslinks. The ligands are MER$_n$ (polymer molecules comprised of n monomeric units) molecules having potential affinity binding capability to selected targets, where n of the ligand polymer (MER from polymer) is in the range of from 2 to about 100 constructed assembled monomeric units, such as polypeptides assembled from amino acids (AAs). Typical ligands employed in the system of this invention are MER$_n$ ligand libraries including polymers having MER-MER links of the following types: amide; urethane; sulfonamide; thiol; thioether; ester; acrylic; and substituted amino (CONX) links. To minimize steric hindrance and promote affinity binding, the ligands are tethered to the HPMP through a single-permanent strong covalent bond so that later displacement of the mating affinity-bound TTM does not sever (hydrolyze) the ligand from the HPMP.

The significance of covalent tethering should not be underestimated. This permits the ligand library to be used repeatedly. The bound libraries of this invention are not destroyed or sacrificed with each affinity screening or probe analysis. The bound libraries of this invention are not destroyed or sacrificed with each affinity screening or probe analysis. The HPMP bound ligand libraries of this invention can be readied for reassay by displacing a prior TTM by washing, e.g., with 0.1 M acid or alkali, or with 6 M urea, concentrated guanidine HCl, a denaturing agent, or the like. The library is then readied for another assay, since these TTM displacement procedures do not sever the ligand/tether bond. Since labeled TTMs are used, it is easy to check that the prior assay TTMs have all been removed.

Examples of alternative tethers include: $C_2$–$C_{30}$ α, ω diaminoalkanes, e.g. 1,3-diaminopropane and 1,6-diaminohexane; a variety of peptides (e.g., oligomers of beta-alanine, aminocaproic acid); polyglycol type derivatives (such as Jeffamine ED-600 from Texaco, O,O'-Bis (2-aminopropyl)-polyethylene glycol 500; and 2,2'-(ethylenedioxy)-diethylamine from Fluka). The presently preferred tether is 1,3-diaminopropane.

The HPMP layer environment is a high accessible (to the TTMs), flexible, 3-D display of the singly tethered ligands providing free permeability therein of the TTMs for affinity binding. The 3-D nature of the HPMP layer provides a highly efficient interaction, between ligands (Ls) and TTMs, and thereby enhanced binding. Compared to flat surface support bound display methods, the 3-D matrix of this invention permits a larger number of MER$_n$s to be displayed for a per given surface area, providing effective amplification of the assay signals.

This invention is unique in being suitable for construction of libraries containing monomer units of almost any kind, for example, bound together by ether, thioether, ester, amine, phosphate, amide or any such bond establishable by organic chemistry methods. Identification is performed solely through spatial recognition, and does not require sequencing, which is generally impossible with other than natural peptide and DNA units. The displayed organic molecules and mixtures thereof, herein broadly called ligands, include but are not limited to, libraries assembled from synthons, such as AA's, nucleotides, mono or bicyclic ring compounds, sugars, most functionalizable organic moieties, and combinations thereof. Other examples of the use of the system includes use with biotin, antihistamines, benzodiazapines, and the like, which bind biological receptors. The availability of libraries of such diverse materials displayed on the system of this invention will significantly expedite discovery of new drugs.

The matrices and methods of the invention are more specifically useful for optimal identification of a binding constituent to any particular biologically relevant protein, but may also be useful in a variety of diagnostic and therapeutic applications. For example, the system may be used for drug delivery. A drug may be tethered by a cleavable linker to an HPMP matrix-coated implant surface, and then under the effect of an endogenous enzyme which acts on the linker, the drug is slowly released, resulting in controlled drug delivery over a long time period.

The system and method of this invention is compatible with a wide range of organic molecules. It not only facilitates their assembly, but also presents them in an essentially 100% aqueous environment, and displays them so that the biological acceptor molecule interacts with them efficiently. It is a particular merit of this invention that the nature of the molecular matrix cuts down interactions between individual displayed ligand molecules. This minimization of environmental effects results in better synthetic efficiencies during assembly of ligands from synthons than prior art systems.

The PILOT ASBCL's and methods of this invention, are therefore unique, simple, generally applicable and readily duplicated. They provide high sensitivity detection by a variety of tagging procedures.

It is important to the application of the PILOT system of this invention as a general library method to equally incorporate amino acids from mixtures of Fmoc-amino acids. We have found that differences in incorporation diminished with increasing concentration, and D-derivatives coupled at rates essentially the same as their L-counterparts.

However, rather than use the Rutter-Santi method of employing concentrations based on the coupling constants of the amino acids, we use a non-theoretical, empirical method of determining the molar ratios for equal incorporation of Fmoc-Amino acids from mixtures. These mixtures are used to prepare the random $X_n$-peptides. We employ 16 AA's to form a standard mixture, $\Omega$. As used herein, Mix•Mix, (Mix)$_2$ or $\Omega$–2 refers to two reaction cycles with the $\Omega$ mixture.

Based on Example 1 below, the molar ratios described in Table 1 below give substantially equal incorporation on HPMP winks as confirmed by both amino acid analysis and sequencing. Sixteen amino acids are incorporated in our standard mixture $\Omega$. Mixtures may be incorporated at 6 or more positions in a core sequence, and "arrayed" at any other two or more positions. Bogus arrays may be constructed using conventional peptide synthesizers. Study of non-arrayed mixed winks in the presence and absence of natural ligand(s) shows whether a detailed array study will be able to uncover binding sequences. The molar ratios of Table 1 are obtained by coupling, AA's selected with 1.25 equivalents HOBt+1.5 equivalents PyBOP and 1.5 equivalents 0.3M NMM in DMF after 10 minutes preactivation.

TABLE I

Molar Ratios For Equal Incoporation of Fmoc—Amino Acids From Mixtures

| Fmoc—Derivative | Molar Ratio | Fmoc—Derivative | Molar Ratio | Fmoc—Derivative | Molar Ratio |
| --- | --- | --- | --- | --- | --- |
| L—Nle* | 1.00 | L—Ala* | 0.79 | D—Nap* | 1.50 |
| L—Leu | 1.00 | L—Ser(tBu)* | 1.50 | L—Tyr(tBu)* | 1.70 |
| L—Val* | 1.60 | L—His(Trt)* | 2.10 | L—Phe* | 1.00 |
| Gly* | 0.60 | L—Gln(Trt)* | 2.20 | L—Asp(OtBu)* | 1.40 |
| D—Ala* | 0.79 | L—Pro* | 1.15 | L—Glu(OtBu)* | 1.20 |
| L—Lys(tBoc)* | 1.36 | L—Arg(Pmc)* | 3.00 | L—Thr(tBu) | 2.00 |
| L—Asn(Trt) | 2.45 | | | | |

"Nap" is 3-(2-naphthyl)-alanine; the 1-naphthyl derivative couples similarly. The AAs marked with * are used in the $\Omega$ mixture.

DETAILED DESCRIPTION OF THE BEST MODE OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Figures 8A, 8B:
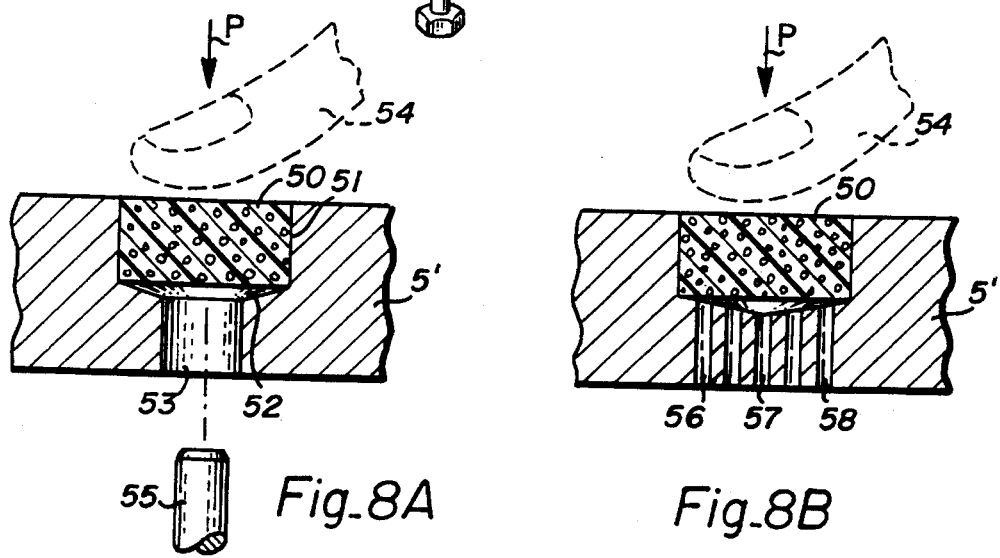
FIG. 8A is an enlarged vertical section view through one hole of the vacuum block with a single vacuum draw and drain hole below the sintered disc "wink" in place in an array hole.
FIG. 8B is a vertical section-view through an alternate embodiment of the vacuum plate with multiple vacuum/drain holes.

Referring to FIG. 1 the slotted block system of this invention 1 includes a base 2 which has or receives orienting members, such as a plurality of guide and securing rods 3 with wing nuts 4. The base 2 receives a square substrate support plate 5 which includes an array of areas 6. There are three basic variations in the substrates: in situ beads, film, or discs as shown in FIGS. 2a, 2b and 8a/8b, repectively.

In a first, embodiment shown in FIG. 2a, each area 6 includes substrate 7 (in this case beads) secured in depression 8 by a suitable glue 9. The second embodiment of FIG. 2b shows a grafted polymeric film as the substrate 7 in depression 8. In both FIGS. 2a and 2b, the substrate carrier plate is shown as a one-piece, or unitary, structure. The discrete addressable sites 6 which provide the individually addressable locations for biopolymer assembly result from depressions, holes, or wells 8 formed in the substrate carrier plate, thus making these discrete depressions or wells unitary or integral to the support plate. As shown in FIGS. 2a and 2b, each discrete addressable area 6 is isolated, or independent, one from another (i.e., they are discrete). The spatially ordered proximity of a plurality of discrete sites forms an array. As can also be seen in FIGS. 2a, 2b, 8a, and 8b, the substrate material 7 is restricted within the depression or well 8 of each addressable site 6 being bounded by the sides of the well. By confining a substrate material to remain wholly within the boundary of its particular well, each discrete substrate 7 is isolated one from the other. FIGS. 8a and 8b show the porous sintered polyolefin HPMP coated disc, which is the presently preferred embodiment.

Overlying the substrate support plate 5 is a square gasket 10, preferably a sheet of chemically inert elastomeric material (e.g., Viton or silicon rubber), having an array of holes 11 therethrough which are the same size as and in alignment with the substrate areas 6. See FIGS. 1, 2a, 2b, 3, 5, 6 and 9. The gasket functions to prevent leakage between individual substrate areas 6 or discs 50. An alternative slotted gasket 10a, shown in FIG. 9 may be used in place of multi-holed gasket 10, but it must be rotated with the slotted block 12. The slotted gasket 10a may be glued to the underside of the slotted block 12. Still another alternative is to provide O-rings, one per array area, in a groove concentrically surrounding each area. Or a groove can be provided on the underside of each slotted block surrounding each slot, which groove receives a round (in cross-section) seal strip.

A square slotted block 12, having holes 13 therethrough to receive the guide/securing rods 3 is placed over the gasket 10. This block 12 includes a plurality of slots 14, 15, 16 etc. therein, which are aligned with and extend a full row width of the substrate areas 6. The slots may be identified, as by the alpha designations A,B,C etc. shown. Note in the substrate support plate 5, additional corresponding rows L,M,N . . . are shown. In a typical block 12, there will be some 10 to 400 such slots. Fastening the wingnuts 4 secures the assembly together in the proper orientation and prevents leakage between adjacent slots and substrate areas when individual reaction solutions are placed in the wells formed by the slots. FIG. 6, the presently preferred embodiment in which the wink carrier plate 5' is used, employs the same top gasket 10, but uses a hole-less bottom gasket 49 to seal between adjacent holes.

Continuing with FIG. 1, after reaction, removal of solution, washing and deprotecting, the block 12 is rotated by 90° and selected solutions are introduced in the chosen slots, to produce a known array of dipeptide sequences. This cycle can be carried out with the apparatus of FIG. 6 as well.

FIG. 3 shows an important variation involving a round substrate support plate 20 having a concentric/radial array 21 of discrete substrate areas or holes 6. A gasket 22 also includes a corresponding concentric/radial array of holes 23. In this embodiment, two slotted plates may be employed sequentially: slotted radial plate 24, and concentric slotted plate 25, in either sequence, 24, 25 or 25, 24. There may be fewer radial slots 26 than the radial array of holes 23 or substrate areas 21, in which case the block 24 may be turned between application of reactants (e.g., AA solutions). The inner concentric segments 27, 28, 29 etc. may be secured in spaced relationship by horizontal rods 30, 31, which are spaced above the bottom 32 of block 25 to insure access of solution to all relevant substrate areas. In FIG. 2 the base plate and pins are omitted for clarity.

FIG. 4 shows in vertical cross section the construction of the concentric slotted plate 25 in which outer ring 33 is spaced from inner core 34 by rod 31. A series of tubular spacers 35, 36, 37, 38 on rod 31 space the concentric intermediate rings 27, 28, 29 to provide concentric annular slots. The rod 31 may be countersunk in bore 39.

FIGS. 5 and 7 show a border frame assembly for functionalizing the substrate areas 8 on support plate 5, e.g., with common AAs, or mixtures of AAs, and for deblocking, washing, probing (screening) and addition of spacer arm derivatives. An edge gasket 40 is placed on the substrate plate 5, then a border frame 41 is placed thereover and secured with clamps 42, 43. This provides a central well 45 for the entire array for simultaneously receiving the appropriate solutions for the functionalizing chemistry.

FIG. 7 shows a border frame assembly in association with a vacuum base 46. In this embodiment the wink carrier plate 5' is sandwiched between two identical edge or periphery gaskets 40a, 40b and placed on vacuum base 46 having a trough-shaped interior cavity 47 and an aspiration outlet tube 48. The border frame 41 is placed on top of gasket 40a and the entire assembly clamped together, by rods 3 through holes 13 which are secured by wingnuts 4. This is the preferred assembly for common steps, e.g., of adding the previously determined or selected di, tetra-, hexa-, etc. peptides and for deprotecting, washing and probing. The tube 48 is connected to a vacuum source, such as a water aspirator, which sucks excess or spent solution through the porous granular sintered winks (see FIGS. 8a and 8b) and out trough 47.

FIGS. 8a and 8b are enlarged vertical section views of the porous HPMP winks 50 (described above and in our co-pending Serial No. 08/019,725) which are easily insertable in holes 51 bored partway through carrier plate 5'. A slight tapered shoulder 52 permits drainage via hole 53 when suction is applied from below. The wink diameter is typically ¼", and hole 53 is ⅛". Pressure P from finger 54 is sufficient to press-fit the winks 50 into holes 5'. A dowel or Q-tip 55 inserted in hole 53 is sufficient to remove the wink. FIG. 8b shows a variation in which multiple drain holes 56, 57, 58 etc. may be employed. A smaller dowel or comb-like pusher may be used to remove the winks by insertion through holes 56–58.

The wink carrier plate 5' securely holds porous polyolefin discs 50 throughout the course of the array and probing. Dextrainized winks are prepared according to Serial No. 08/019,725. Common unarrayed sequences are assembled on the winks using commercial synthesizers. They are then mounted in plate 5' as shown in FIG. 8a. To directly perform an array the plate is mounted in the slotted block apparatus of FIG. 6 with a solid viton gasket 49 between it and the base plate, and a regular holed gasket 10 placed between the plate 5' and the slotted block 12. Coupling of one dimension of the array is then performed. The plate is then transferred to and secured in the vacuum base apparatus of FIG. 7, along with edge gaskets 40a and 40b, and the window frame block 41, and washed with DMF (e.g., shaken with DMF for 30 seconds) then the wash is removed by aspiration through the base 46. This washing is extremely efficient in comparison to the bath technique of FIG. 1. This is followed by Fmoc removal steps (deprotection), and more washings performed analogously. The second dimension of the array may then be performed, or common sequences introduced, as required.

Following assembly of the array, the completed plate mounted in the vacuum block of FIG. 7 is treated with TFA+ scavengers to remove side-chain protection. Following washing with methanol, DMF and water, the plate is then washed and thoroughly equilibrated with assay buffer. The radio-labelled protein is then introduced, and the plate probed as appropriate (10 minutes to 2 hours). A parallel plate produced in a second apparatus of FIG. 7 can be used to simultaneously determine the specificity of binding (i.e., by addition of natural ligand). After incubation, the plate 5' is suction washed rapidly with 4 additions of buffer (20 mL), removing unbound label. Binding may be determined by autoradiography. With weaker isotopes, the individual winks may be punched into scintillation vials and counted. This is a simple and quantitative procedure. Of great importance, we have found that, in a variety of cases, the winks can be recovered, the radioactivity displaced, and the winks reused for similar or different assay purposes. The reusability of the system is one of its key attributes.

The following example protocols describe the sequential steps of the method:

EXAMPLE 1

Determination of AA Mixture Proportions for Equimolar Incorporation on Substrates - Empirical Method The component amino acid (Fmoc-X-OH,1 equivalent) is mixed with Fmoc-Nle-OH (1 equivalent), then dissolved and activated by the addition of PyBOP, HOBt and NMM solutions. After 10 minutes the mixture is added to Nva-PAL-Pepsyn K support (5 mg). After 2 hours the support is washed with DMF repeatedly, treated with 30% piperidine in DMF (to remove incorporated Fmoc- groups), washed with DMF, and methanol, then treated with TFA/water (95:5) for 2 hours. The TFA solution is expelled into a vial, a known proportion of it dried down in vacuo, and the resultant mixed dipeptides X-Nva and Nle-Nva are hydrolysed with 6M HCl at 150 degrees for 1 hour. The relative incorporations of X and Nva are then determined by amino acid analysis.

A graph is constructed plotting molar % X (in this initial round X is 50%) against molar percentage incorporated; and the curve which results when using extremities points at 0 and 100% is used to predict what molar percent X would give equal incorporation to that of Nle. The molar percent incorporation of an individual amino acid is the amount of the amino acid divided by the sum of the amino acid+ Norleucine+Norvaline (i.e., AA/(AA+NLE+NOR)=% incorporation). As shown in FIG. 10 the molar percent incorporation is then plotted against the percent amino acid in the mixture. The zero and 100% data points are also included. Draw a line from the 50 percent point on the y-axis to the curve and then drop a line from that point to the x-axis and determine the percent molar incorporation necessary to obtain a 50 percent amino acid mix. In this example, the first evaluation was made with 50% Asparagine and 50% Norleucine. This gave a mixture of approximately 30% Asparagine and 70% Norleucine. A refined evaluation was made with 67% Asparagine which gave a mix of 45% Asparagine/ 55% Norleucine. The final value was determined to be 71% Aspargine to achieve a 50% mix.

The process is repeated using the predicted molar percent X to confirm and, if necessary, iteratively refine the molar percent. This method has been applied to all 20 natural L-amino acids, most D-amino acids, and several unnatural amino acids, such as beta-alanine and 2-napthylalanine.

For any desired library mixture, the amino acids are selected, mixed in the correct ratios, activated, coupled to the support, and the equal incorporation confirmed by analysis. For the 10 amino acid library the subject of these examples the following recipe gives equal incorporation: Fmoc-L-Nle-OH 0.188 g; Fmoc-L-His(Trt)-OH 0.73 g; Fmoc-L-Pro-OH 0.24 g; Fmoc-L-Gln(Trt)-OH 0.797 g; Fmoc-L-Tyr(tBu)-OH 0.398 g; Fmoc-L-Gly-OH 0.093 g; Fmoc-L-Phe-OH 0.206 g; Fmoc-L-Arg(Pmc)-OH 1.25 g; Fmoc-L-Glu(OtBu)-OH 0.288 g; and Fmoc-D-Ala-OH 0.130 g. To these mixed amino acids were added HOBt 1.614g, and the entire solids totally dissolved in DMF and made up to a volume of 40 mL. For coupling, 10 mL of this solution, called MIX solution, is added to 1.71 g PyBOP reagent, mixed, 0.35 mL of N-methylmorpholine is added, remixed and left for 10 minutes. This solution is adequate to completely cover and react a single 10×10 plate giving equal incorporation. Table I and its related description above show the quantitative amounts in this example converted to molar ratios.

EXAMPLE 2

Preparation of A "Beaded" Plate (Support Plate With Array of Bead-Type Substrate Areas)

The sequence BAla-BAla-BAla-Nle-BAla-Nle-BAla-BAla was assembled on 0.2 mmol/g Pepsyn-K (Millipore) functionalized by treatment with ethylenediamine using a Milligen/Biosearch model 9600 peptide synthesizer using standard BOP+HOBt coupling protocols. Ace Hardware Hot Melt adhesive was cut into thin sections and melted at as low a temperature as possible on a flat PTFE sheet to produce a thin sheet (in a range of from about 0.2 to about 1.0 mm thick) of hot melt adhesive (HMA sheet). The PTFE sheet was removed from the heat, and dry, peptide-bearing Pepsyn-K beads were sprinkled over the melted glue surface and gently patted down. After several hours of cooling, excess beads were removed and the glue sheet lifted off the PTFE sheet, then punched into appropriate circles (e.g. 1–10 mm dia) with a standard hole punch. The resultant discs were then attached to an array of shallow, dished wells in a polyethylene sheet using a Black and Decker Thermogrip glue gun adding a dab of glue in the well and pushing the discs down firmly. The discs can be reinforced with polypropylene or metal mesh. Typically, each patch bears 5 mg of beads, having 1 micromole of spacer arm linked Pepsyn-K. The top right hand corner of every plate is notched or drilled as a reference to prevent the plate being incorrectly aligned at any step.

EXAMPLE 3

A Preparation of A Polymeric "Film" Plate

A 10 mm thick plate of linear high density polyethylene is floated in a water bath at 70° C. and treated with 5M chromium trioxide in 5.3M sulfuric acid for two hours. The plate is washed with water many times, then with methanol, and then with ether, and dried under vacuum. The surface bound carboxylic acids are converted to acid chlorides by treatment with 20% thionyl chloride in chloroform for two hours. The plate is rapidly washed with chloroform, then ether, and dried under a stream of nitrogen and used immediately. This acid chloride functionalized plate can be derivatized by a variety of reagents to introduce many functionalities. Linear polymers, such as polyethylenimine, poly(amino) functionalized polyethylene glycols, and saccharide may be added to the plates by conventional chemistries. For example, for introduction of acryloyl groups, the plate may be treated with either a solution of N-(3-aminopropyl) methacrylamide hydrochloride and triethylamine in DMF, or it may be treated with neat (undiluted) diaminopropane for two hours, followed by washing thoroughly with water, then methanol, then ether, and then treated with a solution of acryloyl chloride and disopropylethyl amine in THF. The plate is washed well consecutively with methanol and ether, and dried under vacuum. The plate is now ready for grafting or casting of a gel film thereon as the substrate in the specific address areas.

The gels which may be cast into the wells of the substrate plate or grafted to the acryloyl groups on the surface of a film plate can have a variety of concentrations, cross-linking levels, functional linkers and amino linker loading. To prepare a typical gel, under nitrogen, a 5 ml portion of deoxygenated water (under vacuum for 20 minutes) is added to 18.5 mg of bisacryloyldiaminohexane, 295 mg of dimethylacrylamide, and 186 mg of the monoacrylamide of 1,6 diaminohexane hydrochloride. This is filtered onto 15 mg of ammonium persulfate and treated with 30 uL of pH 6 TEMED solution in water. In a glove bag under nitrogen, the monomer solution is rapidly transferred to each well of the plate. The plate is sealed in a plastic bag with an open beaker of deoxygenated water and allowed to gel. After curing over night the plate is washed with water and soaked in iN sodium hydroxide for 2 hours. Two water washes of 15 minutes each followed by at least four washes in DMF give a plate which is ready for peptide synthesis.

EXAMPLE 4

Spacer Arm Derivatization of The Film

Optionally a gel film plate of the type in Example 3 may have a tetrapeptide spacer attached to the substrate. A plate prepared as in Example 3 had Fmoc-beta-alanine (BAla) coupled to it (standard PyBOP+HOBt/NMM procedure, 2 hours). Following thorough DMF washes, the plate was treated with 30% piperidine in DMF (1, 45 minutes). The plate was washed 2 times with DMF, and the piperidine treatments and subsequent washes were pooled and read spectrophotometrically at 301 nm to determine the Fmoc-loading (in this example 2 micromoles per substrate area). Three more coupling cycles were then performed adding Fmoc-epsilon-aminocaproic acid twice, then beta-alanine again to give the final BAla-Aca-BAla spacer arm film plate as used in the preferred embodiment for ASBCL or ASPCL libraries.

EXAMPLE 5

Construction of A 10×10 Hexapeptide ASPCL Plate

The method of this invention allows the construction of arrays of sequences at any 2 sequence positions within peptides of any reasonable size with several positions being incorporated as mixtures. The preferred embodiment of the method is to prepare hexapeptides with the central 2 AA's arrayed, the other 4 positions redundantly mixed, and the final sequence AA is N-acetylated. For film plates it is preferred to add a spacer arm peptide to the film prior to construction of the library, and with beaded plates an octapeptide spacer is attached prior to embedding in the glue. The following sequence of operations is followed to prepare a Hexapeptide ASPCL with a known central (3,4) AA sequence:

i) Apply an edge gasket and a border-frame spacer on the substrate plate (see FIG. 5) to make a flat "dish" type reactor. As an alternative to use of the screwed pin base plate assembly of FIG. 1, one may use standard large office clips, or wing nuts and standard bolts and washers to hold the parts together;

ii) Wash with DMF 2x using horizontal action shaker;

iii) Couple 10 mL preactivated MIX solution made as per Example 1 for 2 hours, while covering plate with foil tent;

iv) Wash with DMF 3x;

v) Deblock with 30% piperidine in DMF 1 min, 10 min;

vi) Wash with DMF 5x;

vii) Repeat steps iii) to vi);

viii) Dismount edge gasket and frame spacer, and mount slotted block assembly with 100 hole gasket to base plate as in FIG. 1 with slots in a first, horizontal orientation (L TO R when facing the assembly). DMF solvent is placed in alternate wells and the dry wells observed carefully to ensure no leakage. Prepare in vials the following amino acids: 1. Fmoc-L-Nle-OH 0.14 g; 2. Fmoc-L-His(Trt)-OH 0.25 g; 3. Fmoc-L-Pro-OH 0.135 g; 4. Fmoc-L-Gln(Trt)-OH 0.244 g; 5. Fmoc-Tyr(tBu)OH 0.183 g, 6. Fmoc-Gly-OH 0.116 g; 7. Fmoc-L-Phe-OH 0.154 g; 8. Fmoc-L-Arg(Pmc)-OH 0.265 g; 9. Fmoc-L-Glu(OtBu)-OH 0.17 g; 10. Fmoc-D-Ala-OH 0.124 g. To each of these vials add and mix PyBOP 0.27 g and HOBt 0.06 g, and 2 mL of 0.3M N-methylmorpholine in DMF. Add each to a designated horizontal slot: 1 to top slot; 2 to next slot, etc.;

ix) Maintain at room temperature for 2 hours to complete coupling;

x) Disassemble and remount with edge-gasket and border-frame spacer;

xi) Wash with DMF 3x;

xii) Deprotect with 30% piperidine in DMF 1 minute, 10 minutes;

xiii) Wash with DMF 5x;

xiv) Mount slot block with slots rotated 90°, i.e., in a vertical orientation, and repeat coupling as described in viii) except 1 is coupled to the left hand slot, 2 to the next slot, etc.;

xv) Disassemble and remount with edge-gasket and border-frame spacer;

xvi) Remove Fmoc group and perform 2 cycles of mixture incorporation as described in i) to vii);

xvii) Remove Fmoc-group and wash with DMF 5x;

xviii) Acetylate with 0.3M acetic anhydride+0.3M HOBt in DMF (10 mL) for 1 hour;

xix) Wash DMF 5x, Methanol 5x;

xx) Treat with 95:5 TFA/water for 2 hours;

xxi) Wash Methanol 5x, aqueous buffer 5x. Store in sealed bag at 4 degrees prior to probing to screen a target. Numbering from the carboxy terminus, the resulting hexapeptides are characterized as $XX-A_4$, $A_3-XX$ with the $A_3$ and $A_4$ known sequence being uniquely addressable. That is, the central dipeptide is known from its unique address by use of the slotted block, the hexapeptide at address 001 being XX-D-Ala-L-Nle-XX, at address 002 being XX-L-Glu-L-Nle-XX, etc., to address 100 being XX-L-Nle-D-Ala-XX.

EXAMPLE 6

Construction of A 10×10 Hexapeptide ASPCL on a Gel Film Plate

Instead of a bead plate, a gel film plate as in Examples 3 and 4 may be similarly employed to construct an ASPCL library by the process of Example 5. This gel film ASPCL is used to screen, see Example 7 below.

EXAMPLE 7

Determination of Binding Elements in the Interaction of Streptavidin with Peptides A film library plate of Examples 3 and 4 was constructed similarly to Example 6 with the selection of 10 amino acids as indicated. $^{125}I$ labelled streptavidin was prepared and purified by standard procedures; a fluorescently labelled form was also prepared by reaction of AMCA-NHS (Pierce) with the protein, excess reagent being removed by dialysis. Firstly, the iodinated protein was incubated with the plate overnight in a phosphate buffer containing 150 mM salt, Tween detergent and bovine serum albumin (1 mg/mL). The plate was washed with the buffer 3 times, placed on a standard laboratory X-ray film with an enhancer plate and exposed overnight. The developed film shows strong affinity in specific address locations corresponding to 2 central dipeptides HP and RR. The plate was then washed repeatedly with 6M guanidine hydrochloride, and buffer medium, then reincubated with the fluorescent AMCA-streptavidin overnight. After washing the plate was irradiated with long wave length uv light and visible confirmation obtained of the previously deduced binding elements. Subsequent iterations as described above further defines the active dipeptides at each end for complete hexapeptide characterization.

EXAMPLE 8

Array Test for $^{35}S$ Streptavidin Using HPMP

Winks in a Carrier Plate

This example details the use of the HPMP winks in the carrier plate 5' of FIG. 8a with the slotted block system of FIG. 6 and vacuum base system of FIG. 7.

70 dextran functionalized winks were placed in the reaction vessel of a Millipore Model 9600 peptide synthesizer. A mixture of Fmoc-protected amino acids was made by carefully weighing the individual components according to the following list, followed by intimately mixing them in a pestle and mortar: L-NorLeu, 0.093 g; L-His(Trt), 0.341 g; L-Pro 0.10 g; L-Gln(Trt), 0.351 g; L-Tyr(tBu), 0.203 g; Gly, 0.046 g; L-Phe, 0.102 g; L-Arg(Pmc), 0.52 g; L-Glu(OtBu), 0.132 g; L-Ala, 0.064 g; D-Ala, 0.064 g; L-Asp(OtBu), 0.150 g; L-Val, 0.131 g; L-Ser(tBu), 0.149 g; D-(2-napthyl)Ala, 0.153 g; L-Lys(tBoc), 0.168 g. Four individual aliquots of the mixture (0.461 g) were placed along with PyBOP (0.82 g) and HOBt(0.2 g) in each of the first 4 reservoirs of the instrument, and synthesis performed using standard Fmoc 4 hour coupling programs with 10 minute preactivation.

Following synthesis, 64 of the product winks, now bearing tetrapeptide mixtures of all possible combinations, were placed in an 8×8 array in the standard 10×10 plate with blank winks occupying peripheral positions. The plate was marked in its top right hand corner, washed with DMF several times, then placed in the slotted block system of FIG. 6 with a solid viton gasket between it and the base plate. The standard 100 hole top gasket was then positioned, followed by the slotted block in a vertical orientation. The slots were tested to make sure no leakage was occurring. For array coupling, pairs of amino acids were added to the 8 appropriate slots as follows (each pair also had added 0.80 g PyBOP and 0.2 g HOBt, activation was with 5 mL of 0.3M NMM in DMF): - Slot 2, Tyr(tBu) 0.29 g+Phe 0.143 g; Slot 3, Asp (OtBu) 0.22 g+Glu (OtBu) 0.195 g; Slot 4, Arg(Pmc) 0.457 g+Lys(tBoc) 0.145 g; Slot 5, Nle 0.134 g+Val 0.21 g, Slot 6, Gly 0.128 g+D-Ala 0.177 g; Slot 7, Ala 0.109 g+Ser(tBu) 0.249 g; Slot 8, His(Trt) 0.29 g+Gln(Trt) 0.312 g; Slot 9, Pro 0.146 g+DNapAla 0.25 g. The apparatus was left to gently shake overnight to insure coupling.

The apparatus was disassembled, the plate 5' placed in the vacuum block assembly of FIG. 7, washed with DMF (6x), deblocked with 30% piperidine in DMF for 10 minutes, washed DMF (6x). Plate 5' was placed back in the slotted block system of FIG. 6 with the slotted block being turned 90°. An identical array coupling was performed except that the slots were now oriented in a horizontal manner. After a 4 hour coupling, the plate 5' was transferred back to the vacuum base apparatus of FIG. 7, washed with DMF (6x), deblocked with 30% piperidine in DMF (10 minutes), then washed with DMF (6x) and methanol (6x). The plate 5' carrying the winks was then treated to remove all side-chain protecting groups for 4 hours with 90% TFA, 5% anisole, 2.5% water, 2.5% dimethyl sulfide. Subsequently it was washed 6 times with methanol, then DMF, water, methanol and water. It was then equilibrated overnight in the assay buffer consisting of phosphate buffered saline (PBS) containing 0.2% Tween 20 detergent and 1 mg/mL of bovine serum albumin.

To probe the plate, fresh buffer was added (20 mL), and 100 microliters of standard Amersham $^{35}$S labeled streptavidin solution added. The probing was rocked gently for 2 hours, then the supernatant sucked out via the vacuum base. The plate was then washed rapidly whilst rocking with 2×20 mL of assay buffer, then 2×20 mL of water. The plate was then separated from the apparatus, inverted, and individual winks poked (FIG. 8a) out into clearly labeled corresponding scintillation vials containing 0.5 mL of 0.1M HCl. These vials were shaken for 1 hour to displace bound activity. Standard scitillation cocktail (10 mL) was added, then each vial counted for 5 minutes on a Beckman beta-counter.

Results according to array location are depicted in FIG. 11. Surprisingly, many areas have absorbed radioactivity. Four main peaks were selected, and the 16 possible dipeptides (GF, GY, dAY, dAF, NleG, NleDAla, VG, VdA, NleY, NleF, VY, VF, NleNle, NleV, VNle, VVwere produced on (Mix)$_4$ winks with the aid of a modified multiple peptide synthesizer. Following side-cahin deprotection and probing, VY and VF showed maximal binding with >90% of absorbed counts being displaced with biotin.

A second array series was then performed. (Mix)$_2$ winks were made and mounted in the plate. The array steps were then performed in the central 2 positions of the hexapeptide. First Y, then V were added to complete the process. Deprotection, probing and synthesis of possible selections found VYGF and VYHP as strong binders.

A third array series was then performed with the C-terminal 2 positions arrayed and VYGF appended thereto. Probing showed VYGFRQ as the best combination. Following up a VYHPQ lead, we found VYHPQF and VYHPQV to be good binders, slightly better than HPQFVbA, and our own best sequence HPQVFV. To test whether the two series of peptides overlapped at the biotin binding site of streptavidin, a combination nona-peptide, HPQVYGFRQ, was made and found to be a much stronger binder by both BIAcore and PILOT comparison.

This example illustrates the true potential of the PILOT method for drug discovery. Its high sensitivity, utilizing arrays prepared by the simple system of this invention with optimal display chemistry of the HPMP winks, allows the identification of weak binding elements, which when combined and properly oriented permit advanced pattern recognition for mapping of receptors to yield new highly active drug candidates and high affinity superbinding compounds.

EXAMPLE 9

Comparative Test —TFA Stability of Stapled Dextranized Surfaces Compared to Epichlorohydrin Bonding Winks were dextranized in accord with the methods described above (Sample A). By way of comparative tests, dextran was bonded to polyethylene surfaces using epichlorohydrin (Sample B), as taught by Pharmacia Biosensor AB in connection with the BIAcoret$_{tm}$ surface plasmon resonance biosensor systems (see WO 92/06380, WO 90/05295 and WO 90/05305). Both samples were treated with TFA for various time intervals up to 2 hours. The samples were then analyzed by quantitative sugar loading assays. After only 2 hours, around 90% of dextrans were lost from the epichlorohydrin bonded surfaces, whereas only minor loss (<10%) was detected from the wink surfaces stapled according to the processes of this invention.

It should be understood that various modifications within the scope of this invention can be made by one of ordinary skill in the art without departing from the spirit thereof. We therefore wish our invention to be defined by the scope of the appended claims in view of the specification as broadly as the prior art will permit.

---

SEQUENCE LISTING ( 1 ) GENERAL INFORMATION:

( i i i ) NUMBER OF SEQUENCES: 103

( 2 ) INFORMATION FOR SEQ ID NO: 1:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for Streptavidin Test. Address 1.
    (B) LOCATION:
    (C) IDENTIFICATION METHOD: Constructed using an Arris Pharmaceutical PILOT Support Array System
    (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 1: 1 to 6

(xi) SEQUENCE DESCRIPTION: SEQ ID NO: 1:

Xaa    Xaa    Leu    Ala    Xaa    Xaa
        1                           5

(2) INFORMATION FOR SEQ ID NO: 2:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for Streptavidin Test, Address 2.
    (B) LOCATION:
    (C) IDENTIFICATION METHOD: Constructed using an Arris Pharmaceutical PILOT Support Array System
    (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:

(J) PUBLICATION DATE:
(K) RELEVANT RESIDUES IN SEQ ID NO: 2: 1 to 6

(x i) SEQUENCE DESCRIPTION: SEQ ID NO: 2:

Xaa Xaa Leu Glu Xaa Xaa
1             5

(2) INFORMATION FOR SEQ ID NO: 3:

(i) SEQUENCE CHARACTERISTICS:
(A) LENGTH: 6
(B) TYPE: Amino Acids
(C) STRANDEDNESS:
(D) TOPOLOGY: Linear (i i) MOLECULE TYPE: Peptide
(A) DESCRIPTION:

(i x) FEATURE:
(A) NAME/KEY: 10 x 10 Array Sequence Ligands for Streptavidin Test. Address 3.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 3: 1 to 6

(x i) SEQUENCE DESCRIPTION: SEQ ID NO: 3:

Xaa Xaa Leu Arg Xaa Xaa
1             5

(2) INFORMATION FOR SEQ ID NO: 4:

(i) SEQUENCE CHARACTERISTICS:
(A) LENGTH: 6
(B) TYPE: Amino Acids
(C) STRANDEDNESS:
(D) TOPOLOGY: Linear (i i) MOLECULE TYPE: Peptide
(A) DESCRIPTION:

(i x) FEATURE:
(A) NAME/KEY: 10 x 10 Array Sequence Ligands for Streptavidin Test. Address 4.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO: 4: 1 to 6

( x i ) SEQUENCE DESCRIPTION: SEQ ID NO: 4:

Xaa    Xaa    Leu    Phe    Xaa    Xaa
                    1                            5

( 2 ) INFORMATION FOR SEQ ID NO: 5:

( i ) SEQUENCE CHARACTERISTICS:
                    ( A ) LENGTH: 6
                    ( B ) TYPE: Amino Acids
                    ( C ) STRANDEDNESS:
                    ( D ) TOPOLOGY: Linear ( i i ) MOLECULE TYPE: Peptide
                    ( A ) DESCRIPTION:

( i x ) FEATURE:
                    ( A ) NAME/KEY: 10 x 10 Array Sequence Ligands for
                            Streptavidin Test Address 5.
                    ( B ) LOCATION:
                    ( C ) IDENTIFICATION METHOD: Constructed using an
                            Arris Pharmaceutical PILOT Support Array System
                    ( D ) OTHER INFORMATION: Biological activity unknown.
                            Xaa represents a random amino acid selected from
                            mixtures of the following 10 amino acids to give
                            equal incorporation: Nle, His, Pro, Gln, Tyr, Gly,
                            Phe, Arg, Glu, βAla. Where Leu or Ala is
                            specified at any position in the sequence, then Leu
                            refers to Nle (or normal-leucine) and ala refers to
                            βAla (or beta- alanine).

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO: 5: 1 to 6

( x i ) SEQUENCE DESCRIPTION: SEQ ID NO: 5:

Xaa    Xaa    Leu    Gly    Xaa    Xaa
                    1                            5

( 2 ) INFORMATION FOR SEQ ID NO: 6:

( i ) SEQUENCE CHARACTERISTICS:
                    ( A ) LENGTH: 6
                    ( B ) TYPE: Amino Acids
                    ( C ) STRANDEDNESS:
                    ( D ) TOPOLOGY: Linear ( i i ) MOLECULE TYPE: Peptide
                    ( A ) DESCRIPTION:

( i x ) FEATURE:
                    ( A ) NAME/KEY: 10 x 10 Array Sequence Ligands for
                            Streptavidin Test Address 6.
                    ( B ) LOCATION:
                    ( C ) IDENTIFICATION METHOD: Constructed using an Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 6: 1 to 6

( x i ) SEQUENCE DESCRIPTION: SEQ ID NO: 6:

Xaa     Xaa     Leu     Tyr     Xaa     Xaa
                    1                               5

( 2 ) INFORMATION FOR SEQ ID NO: 7:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test. Address 7.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 7: 1 to 6

( x i ) SEQUENCE DESCRIPTION: SEQ ID NO: 7:

Xaa     Xaa     Leu     Gln     Xaa     Xaa
                    1                               5

( 2 ) INFORMATION FOR SEQ ID NO: 8:

( i ) SEQUENCE CHARACTERISTICS:
            ( A ) LENGTH: 6
            ( B ) TYPE: Amino Acids
            ( C ) STRANDEDNESS:

(D) TOPOLOGY: Linear (i i) MOLECULE TYPE: Peptide
    (A) DESCRIPTION:

(i x) FEATURE:
    (A) NAME/KEY: 10 x 10 Array Sequence Ligands for
        Streptavidin Test. Address 8.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 8: 1 to 6

(x i) SEQUENCE DESCRIPTION: SEQ ID NO: 8:

Xaa    Xaa    Leu    Pro    Xaa    Xaa
    1                                        5

(2) INFORMATION FOR SEQ ID NO: 9:

(i) SEQUENCE CHARACTERISTICS:
    (A) LENGTH: 6
    (B) TYPE: Amino Acids
    (C) STRANDEDNESS:
    (D) TOPOLOGY: Linear (i i) MOLECULE TYPE: Peptide
    (A) DESCRIPTION:

(i x) FEATURE:
    (A) NAME/KEY: 10 x 10 Array Sequence Ligands for
        Streptavidin Test. Address 9.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 9: 1 to 6

(x i) SEQUENCE DESCRIPTION: SEQ ID NO: 9:

Xaa    Xaa    Leu    His    Xaa    Xaa
         1                           5

( 2 ) INFORMATION FOR SEQ ID NO: 10:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test. Address 10.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 10: 1 to 6

( x i ) SEQUENCE DESCRIPTION: SEQ ID NO: 10:

Xaa    Xaa    Leu    Leu    Xaa    Xaa
         1                           5

( 2 ) INFORMATION FOR SEQ ID NO: 11:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test. Address 011.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:

( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 11: 1 to 6

( x i ) SEQUENCE DESCRIPTION: SEQ ID NO: 11:

Xaa  Xaa  His  Ala  Xaa  Xaa
1                    5

( 2 ) INFORMATION FOR SEQ ID NO: 12:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 x 10 Array Sequence Ligands for
Streptavidin Test. Address 12.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 12: 1 to 6

( x i ) SEQUENCE DESCRIPTION: SEQ ID NO: 12:

Xaa  Xaa  His  Glu  Xaa  Xaa
1                    5

( 2 ) INFORMATION FOR SEQ ID NO: 13:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 x 10 Array Sequence Ligands for
Streptavidin Test. Address 13.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly, Phe, Arg, Glu, βAla. Where Leu or Ala is
specified at any position in the sequence, then Leu
refers to Nle (or normal-leucine) and Ala refers to
βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 13: 1 to 6

( x i ) SEQUENCE DESCRIPTION: SEQ ID NO: 13:

Xaa    Xaa    His    Arg    Xaa    Xaa
    1                                                5

( 2 ) INFORMATION FOR SEQ ID NO: 14:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
              Streptavidin Test. Address 14.
        ( B ) LOCATION:
        ( C ) IDENTIFICATION METHOD: Constructed using an
              Arris Pharmaceutical PILOT Support Array System
        ( D ) OTHER INFORMATION: Biological activity unknown.
              Xaa represents a random amino acid selected from
              mixtures of the following 10 amino acids to give
              equal incorporation: Nle, His, Pro, Gln, Tyr, Gly,
              Phe, Arg, Glu, βAla. Where Leu or Ala is
              specified at any position in the sequence, then Leu
              refers to Nle (or normal-leucine) and Ala refers to
              βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 14: 1 to 6

( x i ) SEQUENCE DESCRIPTION: SEQ ID NO: 14:

Xaa    Xaa    His    Phe    Xaa    Xaa
    1                                                5

( 2 ) INFORMATION FOR SEQ ID NO: 15:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test. Address 15.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 15: 1 to 6

( x i ) SEQUENCE DESCRIPTION: SEQ ID NO: 15:

Xaa    Xaa    His    Gly    Xaa    Xaa
        1                                           5

( 2 ) INFORMATION FOR SEQ ID NO: 16:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test. Address 16.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 16: 1 to 6

( x i ) SEQUENCE DESCRIPTION: SEQ ID NO: 16:

Xaa    Xaa    His    Tyr    Xaa    Xaa
        1                                           5

( 2 ) INFORMATION FOR SEQ ID NO: 17:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 x 10 Array Sequence Ligands for
        Streptavidin Test. Address 17.
    ( B ) LOCATION:
    ( C ) IDENTIFICATION METHOD: Constructed using an
        Arris Pharmaceutical PILOT Support Array System
    ( D ) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 17: 1 to 6

( x i ) SEQUENCE DESCRIPTION: SEQ ID NO: 17:

Xaa    Xaa    His    Gln    Xaa    Xaa
    1                                              5

( 2 ) INFORMATION FOR SEQ ID NO: 18:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test. Address 18.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:

```
              ( J ) PUBLICATION DATE:
              ( K ) RELEVANT RESIDUES IN SEQ ID NO: 18: 1 to 6

( x i ) SEQUENCE DESCRIPTION: SEQ ID NO: 18:

Xaa     Xaa     His     Pro     Xaa     Xaa
                  1                                5
```

( 2 ) INFORMATION FOR SEQ ID NO: 19:

```
        ( i ) SEQUENCE CHARACTERISTICS:
              ( A ) LENGTH: 6
              ( B ) TYPE: Amino Acids
              ( C ) STRANDEDNESS:
              ( D ) TOPOLOGY: Linear ( i i ) MOLECULE TYPE: Peptide
              ( A ) DESCRIPTION:

( i x ) FEATURE:
              ( A ) NAME/KEY: 10 x 10 Array Sequence Ligands for
                    Streptavidin Test. Address 19.
              ( B ) LOCATION:
              ( C ) IDENTIFICATION METHOD: Constructed using an
                    Arris Pharmaceutical PILOT Support Array System
              ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
              ( A ) AUTHORS:
              ( B ) TITLE:
              ( C ) JOURNAL:
              ( D ) VOLUME:
              ( E ) ISSUE:
              ( F ) PAGES:
              ( G ) DATE:
              ( H ) DOCUMENT NUMBER:
              ( I ) FILING DATE:
              ( J ) PUBLICATION DATE:
              ( K ) RELEVANT RESIDUES IN SEQ ID NO: 19: 1 to 6

( x i ) SEQUENCE DESCRIPTION: SEQ ID NO: 19:

Xaa     Xaa     His     His     Xaa     Xaa
                  1                                5
```

( 2 ) INFORMATION FOR SEQ ID NO: 20:

```
        ( i ) SEQUENCE CHARACTERISTICS:
              ( A ) LENGTH: 6
              ( B ) TYPE: Amino Acids
              ( C ) STRANDEDNESS:
              ( D ) TOPOLOGY: Linear ( i i ) MOLECULE TYPE: Peptide
              ( A ) DESCRIPTION:

( i x ) FEATURE:
              ( A ) NAME/KEY: 10 x 10 Array Sequence Ligands for
                    Streptavidin Test. Address 20.
              ( B ) LOCATION:
              ( C ) IDENTIFICATION METHOD: Constructed using an
                    Arris Pharmaceutical PILOT Support Array System
              ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).
```

( x ) PUBLICATION INFORMATION:
       ( A ) AUTHORS:
       ( B ) TITLE:
       ( C ) JOURNAL:
       ( D ) VOLUME:
       ( E ) ISSUE:
       ( F ) PAGES:
       ( G ) DATE:
       ( H ) DOCUMENT NUMBER:
       ( I ) FILING DATE:
       ( J ) PUBLICATION DATE:
       ( K ) RELEVANT RESIDUES IN SEQ ID NO: 20: 1 to 6

( x i ) SEQUENCE DESCRIPTION: SEQ ID NO: 20:

```
        Xaa    Xaa    His    Leu    Xaa    Xaa
        1                           5
```

( 2 ) INFORMATION FOR SEQ ID NO: 21:

( i ) SEQUENCE CHARACTERISTICS:
       ( A ) LENGTH: 6
       ( B ) TYPE: Amino Acids
       ( C ) STRANDEDNESS:
       ( D ) TOPOLOGY: Linear ( i i ) MOLECULE TYPE: Peptide
       ( A ) DESCRIPTION:

( i x ) FEATURE:
       ( A ) NAME/KEY: 10 x 10 Array Sequence Ligands for
            Streptavidin Test. Address 21.
       ( B ) LOCATION:
       ( C ) IDENTIFICATION METHOD: Constructed using an
            Arris Pharmaceutical PILOT Support Array System
       ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
       ( A ) AUTHORS:
       ( B ) TITLE:
       ( C ) JOURNAL:
       ( D ) VOLUME:
       ( E ) ISSUE:
       ( F ) PAGES:
       ( G ) DATE:
       ( H ) DOCUMENT NUMBER:
       ( I ) FILING DATE:
       ( J ) PUBLICATION DATE:
       ( K ) RELEVANT RESIDUES IN SEQ ID NO: 21: 1 to 6

( x i ) SEQUENCE DESCRIPTION: SEQ ID NO: 21:

```
        Xaa    Xaa    Pro    Ala    Xaa    Xaa
        1                           5
```

( 2 ) INFORMATION FOR SEQ ID NO: 22:

( i ) SEQUENCE CHARACTERISTICS:
       ( A ) LENGTH: 6
       ( B ) TYPE: Amino Acids
       ( C ) STRANDEDNESS:
       ( D ) TOPOLOGY: Linear ( i i ) MOLECULE TYPE: Peptide
       ( A ) DESCRIPTION:

( i x ) FEATURE:
       ( A ) NAME/KEY: 10 x 10 Array Sequence Ligands for
            Streptavidin Test. Address 22.
       ( B ) LOCATION:
       ( C ) IDENTIFICATION METHOD: Constructed using an Arris Pharmaceutical PILOT Support Array System
- (D) OTHER INFORMATION: Biological activity unknown.
  Xaa represents a random amino acid selected from
  mixtures of the following 10 amino acids to give
  equal incorporation: Nle, His, Pro, Gln, Tyr, Gly,
  Phe, Arg, Glu, βAla. Where Leu or Ala is
  specified at any position in the sequence, then Leu
  refers to Nle (or normal-leucine) and Ala refers to
  βAla (or beta- alanine).

(x) PUBLICATION INFORMATION:
- (A) AUTHORS:
- (B) TITLE:
- (C) JOURNAL:
- (D) VOLUME:
- (E) ISSUE:
- (F) PAGES:
- (G) DATE:
- (H) DOCUMENT NUMBER:
- (I) FILING DATE:
- (J) PUBLICATION DATE:
- (K) RELEVANT RESIDUES IN SEQ ID NO: 22: 1 to 6

(xi) SEQUENCE DESCRIPTION: SEQ ID NO: 22:

```
Xaa   Xaa   Pro   Glu   Xaa   Xaa
1                       5
```

(2) INFORMATION FOR SEQ ID NO: 23:

- (i) SEQUENCE CHARACTERISTICS:
  - (A) LENGTH: 6
  - (B) TYPE: Amino Acids
  - (C) STRANDEDNESS:
  - (D) TOPOLOGY: Linear

- (ii) MOLECULE TYPE: Peptide
  - (A) DESCRIPTION:

- (ix) FEATURE:
  - (A) NAME/KEY: 10 x 10 Array Sequence Ligands for
    Streptavidin Test. Address 23.
  - (B) LOCATION:
  - (C) IDENTIFICATION METHOD: Constructed using an
    Arris Pharmaceutical PILOT Support Array System
  - (D) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, βAla. Where Leu or Ala is
    specified at any position in the sequence, then Leu
    refers to Nle (or normal-leucine) and Ala refers to
    βAla (or beta- alanine).

- (x) PUBLICATION INFORMATION:
  - (A) AUTHORS:
  - (B) TITLE:
  - (C) JOURNAL:
  - (D) VOLUME:
  - (E) ISSUE:
  - (F) PAGES:
  - (G) DATE:
  - (H) DOCUMENT NUMBER:
  - (I) FILING DATE:
  - (J) PUBLICATION DATE:
  - (K) RELEVANT RESIDUES IN SEQ ID NO: 23: 1 to 6

(xi) SEQUENCE DESCRIPTION: SEQ ID NO: 23:

```
Xaa   Xaa   Pro   Arg   Xaa   Xaa
1                       5
```

(2) INFORMATION FOR SEQ ID NO:24:

- (i) SEQUENCE CHARACTERISTICS:
  - (A) LENGTH: 6
  - (B) TYPE: Amino Acids
  - (C) STRANDEDNESS:

( D ) TOPOLOGY: Linear ( i i ) MOLECULE TYPE: Peptide
                ( A ) DESCRIPTION:

( i x ) FEATURE:
                ( A ) NAME/KEY: 10 x 10 Array Sequence Ligands for
                        Streptavidin Test Address 24.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, βAla. Where Leu or Ala is
                        specified at any position in the sequence, then Leu
                        refers to Nle (or normal-leucine) and Ala refers to
                        βAla (or beta- alanine).

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO: 24: 1 to 6

( x i ) SEQUENCE DESCRIPTION: SEQ ID NO: 24:

Xaa     Xaa     Pro     Phe     Xaa     Xaa
                        1                               5

( 2 ) INFORMATION FOR SEQ ID NO:25:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 x 10 Array Sequence Ligands for
                        Streptavidin Test Address 25.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, βAla. Where Leu or Ala is
                        specified at any position in the sequence, then Leu
                        refers to Nle (or normal-leucine) and Ala refers to
                        βAla (or beta- alanine).

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO: 25: 1 to 6

( x i ) SEQUENCE DESCRIPTION: SEQ ID NO: 25:

Xaa   Xaa   Pro   Gly   Xaa   Xaa
            1                       5

( 2 ) INFORMATION FOR SEQ ID NO: 26:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test. Address 26.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 26: 1 to 6

( x i ) SEQUENCE DESCRIPTION: SEQ ID NO: 26:

Xaa   Xaa   Pro   Tyr   Xaa   Xaa
            1                       5

( 2 ) INFORMATION FOR SEQ ID NO:27:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test. Address 27
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:

( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 27: 1 to 6

( x i ) SEQUENCE DESCRIPTION: SEQ ID NO: 27:

Xaa   Xaa   Pro   Gln   Xaa   Xaa
1                       5

( 2 ) INFORMATION FOR SEQ ID NO: 28:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 x 10 Array Sequence Ligands for Streptavidin Test. Address 28.
( B ) LOCATION:
( C ) IDENTIFICATION METHOD: Constructed using an Arris Pharmaceutical PILOT Support Array System
( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 28: 1 to 6

( x i ) SEQUENCE DESCRIPTION: SEQ ID NO: 28:

Xaa   Xaa   Pro   Pro   Xaa   Xaa
1                       5

( 2 ) INFORMATION FOR SEQ ID NO: 29:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 x 10 Array Sequence Ligand for Streptavidin Test, Address 29.
( B ) LOCATION:
( C ) IDENTIFICATION METHOD: Constructed using an Arris Pharmaceutical PILOT Support Array System
( D ) OTHER INFORMATION: Exhibits specific binding activity with Streptavidin. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 29: 1 to 6

( x i ) SEQUENCE DESCRIPTION: SEQ ID NO: 29:

```
Xaa    Xaa    Pro    His    Xaa    Xaa
 1                           5
```

( 2 ) INFORMATION FOR SEQ ID NO: 30:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for Streptavidin Test, Address 30.
        ( B ) LOCATION:
        ( C ) IDENTIFICATION METHOD: Constructed using an Arris Pharmaceutical PILOT Support Array System
        ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 30: 1 to 6

( x i ) SEQUENCE DESCRIPTION: SEQ ID NO: 30:

```
Xaa    Xaa    Pro    Leu    Xaa    Xaa
 1                           5
```

( 2 ) INFORMATION FOR SEQ ID NO: 31:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
- ( A ) NAME/KEY: 10 x 10 Array Sequence Ligands for
  Streptavidin Test, Address 31.
- ( B ) LOCATION:
- ( C ) IDENTIFICATION METHOD: Constructed using an
  Arris Pharmaceutical PILOT Support Array System
- ( D ) OTHER INFORMATION: Biological activity unknown.
  Xaa represents a random amino acid selected from
  mixtures of the following 10 amino acids to give
  equal incorporation: Nle, His, Pro, Gln, Tyr, Gly,
  Phe, Arg, Glu, βAla. Where Leu or Ala is
  specified at any position in the sequence, then Leu
  refers to Nle (or normal-leucine) and Ala refers to
  βAla (or beta- alanine).

( x ) PUBLICATION INFORMATION:
- ( A ) AUTHORS:
- ( B ) TITLE:
- ( C ) JOURNAL:
- ( D ) VOLUME:
- ( E ) ISSUE:
- ( F ) PAGES:
- ( G ) DATE:
- ( H ) DOCUMENT NUMBER:
- ( I ) FILING DATE:
- ( J ) PUBLICATION DATE:
- ( K ) RELEVANT RESIDUES IN SEQ ID NO: 31: 1 to 6

( x i ) SEQUENCE DESCRIPTION: SEQ ID NO: 31:

```
Xaa   Xaa   Gln   Ala   Xaa   Xaa
 1                       5
```

( 2 ) INFORMATION FOR SEQ ID NO: 32:

( i ) SEQUENCE CHARACTERISTICS:
- ( A ) LENGTH: 6
- ( B ) TYPE: Amino Acids
- ( C ) STRANDEDNESS:
- ( D ) TOPOLOGY: Linear ( i i ) MOLECULE TYPE: Peptide
- ( A ) DESCRIPTION:

( i x ) FEATURE:
- ( A ) NAME/KEY: 10 x 10 Array Sequence Ligands for
  Streptavidin Test, Address 32.
- ( B ) LOCATION:
- ( C ) IDENTIFICATION METHOD: Constructed using an
  Arris Pharmaceutical PILOT Support Array System
- ( D ) OTHER INFORMATION: Biological activity unknown.
  Xaa represents a random amino acid selected from
  mixtures of the following 10 amino acids to give
  equal incorporation: Nle, His, Pro, Gln, Tyr, Gly,
  Phe, Arg, Glu, βAla. Where Leu or Ala is
  specified at any position in the sequence, then Leu
  refers to Nle (or normal-leucine) and Ala refers to
  βAla (or beta- alanine).

( x ) PUBLICATION INFORMATION:
- ( A ) AUTHORS:
- ( B ) TITLE:
- ( C ) JOURNAL:
- ( D ) VOLUME:
- ( E ) ISSUE:
- ( F ) PAGES:
- ( G ) DATE:
- ( H ) DOCUMENT NUMBER:
- ( I ) FILING DATE:
- ( J ) PUBLICATION DATE:
- ( K ) RELEVANT RESIDUES IN SEQ ID NO: 32: 1 to 6

( x i ) SEQUENCE DESCRIPTION: SEQ ID NO: 32:

```
Xaa   Xaa   Gln   Glu   Xaa   Xaa
 1                       5
```

( 2 ) INFORMATION FOR SEQ ID NO: 33:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                Streptavidin Test, Address 33.
            ( B ) LOCATION:
            ( C ) IDENTIFICATION METHOD: Constructed using an
                Arris Pharmaceutical PILOT Support Array System
            ( D ) OTHER INFORMATION: Biological activity unknown.
                Xaa represents a random amino acid selected from
                mixtures of the following 10 amino acids to give
                equal incorporation: Nle, His, Pro, Gln, Tyr, Gly,
                Phe, Arg, Glu, βAla. Where Leu or Ala is
                specified at any position in the sequence, then Leu
                refers to Nle (or normal-leucine) and Ala refers to
                βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 33: 1 to 6

( x i ) SEQUENCE DESCRIPTION: SEQ ID NO: 33:

Xaa    Xaa    Gln    Arg    Xaa    Xaa
                1                                            5

( 2 ) INFORMATION FOR SEQ ID NO: 34:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                Streptavidin Test, Address 34.
            ( B ) LOCATION:
            ( C ) IDENTIFICATION METHOD: Constructed using an
                Arris Pharmaceutical PILOT Support Array System
            ( D ) OTHER INFORMATION: Biological activity unknown.
                Xaa represents a random amino acid selected from
                mixtures of the following 10 amino acids to give
                equal incorporation: Nle, His, Pro, Gln, Tyr, Gly,
                Phe, Arg, Glu, βAla. Where Leu or Ala is
                specified at any position in the sequence, then Leu
                refers to Nle (or normal-leucine) and Ala refers to
                βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:

(I) FILING DATE:
(J) PUBLICATION DATE:
(K) RELEVANT RESIDUES IN SEQ ID NO: 34: 1 to 6

(xi) SEQUENCE DESCRIPTION: SEQ ID NO: 34:

Xaa    Xaa    Gln    Phe    Xaa    Xaa
1                          5

(2) INFORMATION FOR SEQ ID NO: 35:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for Streptavidin Test, Address 35.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 35: 1 to 6

(xi) SEQUENCE DESCRIPTION: SEQ ID NO: 35:

Xaa    Xaa    Gln    Gly    Xaa    Xaa
1                          5

(2) INFORMATION FOR SEQ ID NO: 36:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for Streptavidin Test, Address 36.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 36: 1 to 6

( x i ) SEQUENCE DESCRIPTION: SEQ ID NO: 36:

```
Xaa   Xaa   Gln   Tyr   Xaa   Xaa
1                       5
```

( 2 ) INFORMATION FOR SEQ ID NO: 37:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 37.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 37: 1 to 6

( x i ) SEQUENCE DESCRIPTION: SEQ ID NO: 37:

```
Xaa   Xaa   Gln   Gln   Xaa   Xaa
1                       5
```

( 2 ) INFORMATION FOR SEQ ID NO:38:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 38.
        ( B ) LOCATION:

(C) IDENTIFICATION METHOD: Constructed using an
    Arris Pharmaceutical PILOT Support Array System
(D) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, βAla. Where Leu or Ala is
    specified at any position in the sequence, then Leu
    refers to Nle (or normal-leucine) and Ala refers to
    βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 38: 1 to 6

(xi) SEQUENCE DESCRIPTION: SEQ ID NO: 38:

```
Xaa   Xaa   Gln   Pro   Xaa   Xaa
1                       5
```

(2) INFORMATION FOR SEQ ID NO: 39:

(i) SEQUENCE CHARACTERISTICS:
       (A) LENGTH: 6
       (B) TYPE: Amino Acids
       (C) STRANDEDNESS:
       (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for
            Streptavidin Test, Address 39.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

(x) PUBLICATION INFORMATION:
       (A) AUTHORS:
       (B) TITLE:
       (C) JOURNAL:
       (D) VOLUME:
       (E) ISSUE:
       (F) PAGES:
       (G) DATE:
       (H) DOCUMENT NUMBER:
       (I) FILING DATE:
       (J) PUBLICATION DATE:
       (K) RELEVANT RESIDUES IN SEQ ID NO: 39: 1 to 6

(xi) SEQUENCE DESCRIPTION: SEQ ID NO: 39:

```
Xaa   Xaa   Gln   His   Xaa   Xaa
1                       5
```

(2) INFORMATION FOR SEQ ID NO: 40:

(i) SEQUENCE CHARACTERISTICS:
       (A) LENGTH: 6
       (B) TYPE: Amino Acids (C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for
Streptavidin Test, Address 40.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 40: 1 to 6

(xi) SEQUENCE DESCRIPTION: SEQ ID NO: 40:

Xaa   Xaa   Gln   Leu   Xaa   Xaa
 1                       5

(2) INFORMATION FOR SEQ ID NO: 41:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for
Streptavidin Test, Address 41.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 41: 1 to 6

(xi) SEQUENCE DESCRIPTION: SEQ ID NO: 41:

Xaa    Xaa    Tyr    Ala    Xaa    Xaa
                    1                           5

( 2 ) INFORMATION FOR SEQ ID NO: 42:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test, Address 42.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 42: 1 to 6

( x i ) SEQUENCE DESCRIPTION: SEQ ID NO: 42:

Xaa    Xaa    Tyr    Glu    Xaa    Xaa
                    1                           5

( 2 ) INFORMATION FOR SEQ ID NO: 43:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                    Streptavidin Test, Address 43.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, βAla. Where Leu or Ala is
                    specified at any position in the sequence, then Leu
                    refers to Nle (or normal-leucine) and Ala refers to
                    βAla (or beta- alanine).

( x ) PUBLICATION INFORMATION:
            ( A ) AUTHORS:
            ( B ) TITLE:
            ( C ) JOURNAL:

(D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 43: 1 to 6

(x i) SEQUENCE DESCRIPTION: SEQ ID NO: 43:

Xaa   Xaa   Tyr   Arg   Xaa   Xaa
            1                       5

(2) INFORMATION FOR SEQ ID NO: 44:

(i) SEQUENCE CHARACTERISTICS:
        (A) LENGTH: 6
        (B) TYPE: Amino Acids
        (C) STRANDEDNESS:
        (D) TOPOLOGY: Linear (i i) MOLECULE TYPE: Peptide
        (A) DESCRIPTION:

(i x) FEATURE:
        (A) NAME/KEY: 10 x 10 Array Sequence Ligands for
            Streptavidin Test, Address 44.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta-alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 44: 1 to 6

(x i) SEQUENCE DESCRIPTION: SEQ ID NO: 44:

Xaa   Xaa   Tyr   Phe   Xaa   Xaa
            1                       5

(2) INFORMATION FOR SEQ ID NO: 45:

(i) SEQUENCE CHARACTERISTICS:
        (A) LENGTH: 6
        (B) TYPE: Amino Acids
        (C) STRANDEDNESS:
        (D) TOPOLOGY: Linear (i i) MOLECULE TYPE: Peptide
        (A) DESCRIPTION:

(i x) FEATURE:
        (A) NAME/KEY: 10 x 10 Array Sequence Ligands for
            Streptavidin Test, Address 45.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 45: 1 to 6

( x i ) SEQUENCE DESCRIPTION: SEQ ID NO: 45:

```
Xaa    Xaa    Tyr    Gly    Xaa    Xaa
 1                           5
```

( 2 ) INFORMATION FOR SEQ ID NO: 46:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for Streptavidin Test, Address 46.
        ( B ) LOCATION:
        ( C ) IDENTIFICATION METHOD: Constructed using an Arris Pharmaceutical PILOT Support Array System
        ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 46: 1 to 6

( x i ) SEQUENCE DESCRIPTION: SEQ ID NO: 46:

```
Xaa    Xaa    Tyr    Tyr    Xaa    Xaa
 1                           5
```

( 2 ) INFORMATION FOR SEQ ID NO: 47:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
    ( A ) NAME/KEY: 10 x 10 Array Sequence Ligands for
        Streptavidin Test, Address 47.
    ( B ) LOCATION:
    ( C ) IDENTIFICATION METHOD: Constructed using an
        Arris Pharmaceutical PILOT Support Array System
    ( D ) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 47: 1 to 6

( x i ) SEQUENCE DESCRIPTION: SEQ ID NO: 47:

Xaa    Xaa    Tyr    Gln    Xaa    Xaa
    1                                       5

( 2 ) INFORMATION FOR SEQ ID NO: 48:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 x 10 Array Sequence Ligands for
        Streptavidin Test, Address 048.
    ( B ) LOCATION:
    ( C ) IDENTIFICATION METHOD: Constructed using an
        Arris Pharmaceutical PILOT Support Array System
    ( D ) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 48: 1 to 6

( x i ) SEQUENCE DESCRIPTION: SEQ ID NO: 48:

Xaa    Xaa    Tyr    Pro    Xaa    Xaa
    1                                       5

( 2 ) INFORMATION FOR SEQ ID NO: 49:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 49.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 49: 1 to 6

( x i ) SEQUENCE DESCRIPTION: SEQ ID NO: 49:

Xaa    Xaa    Tyr    His    Xaa    Xaa
        1                                              5

( 2 ) INFORMATION FOR SEQ ID NO: 50:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 50.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:

(I) FILING DATE:
(J) PUBLICATION DATE:
(K) RELEVANT RESIDUES IN SEQ ID NO: 50: 1 to 6

(xi) SEQUENCE DESCRIPTION: SEQ ID NO: 50:

Xaa  Xaa  Tyr  Leu  Xaa  Xaa
1                    5

(2) INFORMATION FOR SEQ ID NO: 51:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for Streptavidin Test, Address 51.
    (B) LOCATION:
    (C) IDENTIFICATION METHOD: Constructed using an Arris Pharmaceutical PILOT Support Array System
    (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 51: 1 to 6

(xi) SEQUENCE DESCRIPTION: SEQ ID NO: 51:

Xaa  Xaa  Gly  Ala  Xaa  Xaa
1                    5

(2) INFORMATION FOR SEQ ID NO: 52:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for Streptavidin Test, Address 52.
    (B) LOCATION:
    (C) IDENTIFICATION METHOD: Constructed using an Arris Pharmaceutical PILOT Support Array System
    (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 52: 1 to 6

( x i ) SEQUENCE DESCRIPTION: SEQ ID NO: 52:

Xaa    Xaa    Gly    Glu    Xaa    Xaa
    1                                          5

( 2 ) INFORMATION FOR SEQ ID NO: 53:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 53.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 53: 1 to 6

( x i ) SEQUENCE DESCRIPTION: SEQ ID NO: 53:

Xaa    Xaa    Gly    Arg    Xaa    Xaa
        1                                          5

( 2 ) INFORMATION FOR SEQ ID NO: 54:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 54.
        ( B ) LOCATION:

(C) IDENTIFICATION METHOD: Constructed using an
    Arris Pharmaceutical PILOT Support Array System
(D) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, βAla. Where Leu or Ala is
    specified at any position in the sequence, then Leu
    refers to Nle (or normal-leucine) and Ala refers to
    βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 54: 1 to 6

(x i) SEQUENCE DESCRIPTION: SEQ ID NO: 54:

Xaa   Xaa   Gly   Phe   Xaa   Xaa
    1                       5

(2) INFORMATION FOR SEQ ID NO: 55:

(i) SEQUENCE CHARACTERISTICS:
        (A) LENGTH: 6
        (B) TYPE: Amino Acids
        (C) STRANDEDNESS:
        (D) TOPOLOGY: Linear (i i) MOLECULE TYPE: Peptide
        (A) DESCRIPTION:

(i x) FEATURE:
        (A) NAME/KEY: 10 x 10 Array Sequence Ligands for
            Streptavidin Test, Address 55.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 55: 1 to 6

(x i) SEQUENCE DESCRIPTION: SEQ ID NO: 55:

Xaa   Xaa   Gly   Gly   Xaa   Xaa
        1                       5

(2) INFORMATION FOR SEQ ID NO: 56:

(i) SEQUENCE CHARACTERISTICS:
        (A) LENGTH: 6
        (B) TYPE: Amino Acids (C) STRANDEDNESS:
(D) TOPOLOGY: Linear (i i) MOLECULE TYPE: Peptide
(A) DESCRIPTION:

(i x) FEATURE:
(A) NAME/KEY: 10 x 10 Array Sequence Ligands for
Streptavidin Test, Address 56.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 56: 1 to 6

(x i) SEQUENCE DESCRIPTION: SEQ ID NO: 56:

Xaa    Xaa    Gly    Tyr    Xaa    Xaa
1                          5

(2) INFORMATION FOR SEQ ID NO: 57:

(i) SEQUENCE CHARACTERISTICS:
(A) LENGTH: 6
(B) TYPE: Amino Acids
(C) STRANDEDNESS:
(D) TOPOLOGY: Linear (i i) MOLECULE TYPE: Peptide
(A) DESCRIPTION:

(i x) FEATURE:
(A) NAME/KEY: 10 x 10 Array Sequence Ligands for
Streptavidin Test, Address 57.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 57: 1 to 6

(x i) SEQUENCE DESCRIPTION: SEQ ID NO: 57:

Xaa Xaa Gly Gln Xaa Xaa
1                   5

(2) INFORMATION FOR SEQ ID NO: 58:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for
            Streptavidin Test, Address 58.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 58: 1 to 6

(xi) SEQUENCE DESCRIPTION: SEQ ID NO: 58:

Xaa Xaa Gly Pro Xaa Xaa
1                   5

(2) INFORMATION FOR SEQ ID NO: 59:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for
            Streptavidin Test, Address 59.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

(x) PUBLICATION INFORMATION:
        (A) AUTHORS:
        (B) TITLE:
        (C) JOURNAL:

(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 59: 1 to 6

(xi) SEQUENCE DESCRIPTION: SEQ ID NO: 59:

Xaa    Xaa    Gly    His    Xaa    Xaa
 1                           5

(2) INFORMATION FOR SEQ ID NO: 60:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 60.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 60: 1 to 6

(xi) SEQUENCE DESCRIPTION: SEQ ID NO: 60:

Xaa    Xaa    Gly    Leu    Xaa    Xaa
 1                           5

(2) INFORMATION FOR SEQ ID NO: 61:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 61.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO: 61: 1 to 6

( x i ) SEQUENCE DESCRIPTION: SEQ ID NO: 61:

Xaa    Xaa    Phe    Ala    Xaa    Xaa
 1                           5

( 2 ) INFORMATION FOR SEQ ID NO: 62:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 x 10 Array Sequence Ligands for
          Streptavidin Test, Address 62.
    ( B ) LOCATION:
    ( C ) IDENTIFICATION METHOD: Constructed using an
          Arris Pharmaceutical PILOT Support Array System
    ( D ) OTHER INFORMATION: Biological activity unknown.
          Xaa represents a random amino acid selected from
          mixtures of the following 10 amino acids to give
          equal incorporation: Nle, His, Pro, Gln, Tyr, Gly,
          Phe, Arg, Glu, βAla. Where Leu or Ala is
          specified at any position in the sequence, then Leu
          refers to Nle (or normal-leucine) and Ala refers to
          βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 62: 1 to 6

( x i ) SEQUENCE DESCRIPTION: SEQ ID NO: 62:

Xaa    Xaa    Phe    Glu    Xaa    Xaa
 1                           5

( 2 ) INFORMATION FOR SEQ ID NO: 63:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 x 10 Array Sequence Ligands for Streptavidin Test, Address 63.
    ( B ) LOCATION:
    ( C ) IDENTIFICATION METHOD: Constructed using an Arris Pharmaceutical PILOT Support Array System
    ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 63: 1 to 6

( x i ) SEQUENCE DESCRIPTION: SEQ ID NO: 63:

Xaa    Xaa    Phe    Arg    Xaa    Xaa
    1                                       5

( 2 ) INFORMATION FOR SEQ ID NO: 64:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for Streptavidin Test, Address 64.
        ( B ) LOCATION:
        ( C ) IDENTIFICATION METHOD: Constructed using an Arris Pharmaceutical PILOT Support Array System
        ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 64: 1 to 6

( x i ) SEQUENCE DESCRIPTION: SEQ ID NO: 64:

Xaa    Xaa    Phe    Phe    Xaa    Xaa
    1                                       5

( 2 ) INFORMATION FOR SEQ ID NO: 65:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 65.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 65: 1 to 6

( x i ) SEQUENCE DESCRIPTION: SEQ ID NO: 65:

Xaa    Xaa    Phe    Gly    Xaa    Xaa
        1                                                5

( 2 ) INFORMATION FOR SEQ ID NO: 66:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 66.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:

( I ) FILING DATE:
( J ) PUBLICATION DATE:
( K ) RELEVANT RESIDUES IN SEQ ID NO: 66: 1 to 6

( x i ) SEQUENCE DESCRIPTION: SEQ ID NO: 66:

Xaa    Xaa    Phe    Tyr    Xaa    Xaa
    1                                                                  5

( 2 ) INFORMATION FOR SEQ ID NO: 67:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
              Streptavidin Test, Address 067.
        ( B ) LOCATION:
        ( C ) IDENTIFICATION METHOD: Constructed using an
              Arris Pharmaceutical PILOT Support Array System
        ( D ) OTHER INFORMATION: Biological activity unknown.
              Xaa represents a random amino acid selected from
              mixtures of the following 10 amino acids to give
              equal incorporation: Nle, His, Pro, Gln, Tyr, Gly,
              Phe, Arg, Glu, βAla. Where Leu or Ala is
              specified at any position in the sequence, then Leu
              refers to Nle (or normal-leucine) and Ala refers to
              βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 67: 1 to 6

( x i ) SEQUENCE DESCRIPTION: SEQ ID NO: 67:

Xaa    Xaa    Phe    Gln    Xaa    Xaa
    1                                                                  5

( 2 ) INFORMATION FOR SEQ ID NO: 68:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
              Streptavidin Test, Address 68.
        ( B ) LOCATION:
        ( C ) IDENTIFICATION METHOD: Constructed using an
              Arris Pharmaceutical PILOT Support Array System
        ( D ) OTHER INFORMATION: Biological activity unknown.
              Xaa represents a random amino acid selected from
              mixtures of the following 10 amino acids to give
              equal incorporation: Nle, His, Pro, Gln, Tyr, Gly,
              Phe, Arg, Glu, βAla. Where Leu or Ala is
              specified at any position in the sequence, then Leu
              refers to Nle (or normal-leucine) and Ala refers to
              βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 68: 1 to 6

(xi) SEQUENCE DESCRIPTION: SEQ ID NO: 68:

```
Xaa  Xaa  Phe  Pro  Xaa  Xaa
1                   5
```

(2) INFORMATION FOR SEQ ID NO: 69:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for Streptavidin Test, Address 69.
        (B) LOCATION:
        (C) IDENTIFICATION METHOD: Constructed using an Arris Pharmaceutical PILOT Support Array System
        (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 69: 1 to 6

(xi) SEQUENCE DESCRIPTION: SEQ ID NO: 69:

```
Xaa  Xaa  Phe  His  Xaa  Xaa
1                   5
```

(2) INFORMATION FOR SEQ ID NO: 70:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for Streptavidin Test, Address 070.
        (B) LOCATION:

(C) IDENTIFICATION METHOD: Constructed using an
    Arris Pharmaceutical PILOT Support Array System
(D) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, βAla. Where Leu or Ala is
    specified at any position in the sequence, then Leu
    refers to Nle (or normal-leucine) and Ala refers to
    βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 70: 1 to 6

(xi) SEQUENCE DESCRIPTION: SEQ ID NO: 70:

```
Xaa    Xaa    Phe    Leu    Xaa    Xaa
 1                           5
```

(2) INFORMATION FOR SEQ ID NO: 71:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 71.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 71: 1 to 6

(xi) SEQUENCE DESCRIPTION: SEQ ID NO: 71:

```
Xaa    Xaa    Arg    Ala    Xaa    Xaa
 1                           5
```

(2) INFORMATION FOR SEQ ID NO: 72:

(i) SEQUENCE CHARACTERISTICS:
    (A) LENGTH: 6
    (B) TYPE: Amino Acids ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligands for
                  Streptavidin Test, Address 72.
            ( B ) LOCATION:
            ( C ) IDENTIFICATION METHOD: Constructed using an
                  Arris Pharmaceutical PILOT Support Array System
            ( D ) OTHER INFORMATION: Biological activity unknown.
                  Xaa represents a random amino acid selected from
                  mixtures of the following 10 amino acids to give
                  equal incorporation: Nle, His, Pro, Gln, Tyr, Gly,
                  Phe, Arg, Glu, βAla. Where Leu or Ala is
                  specified at any position in the sequence, then Leu
                  refers to Nle (or normal-leucine) and Ala refers to
                  βAla (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 72: 1 to 6

( x i ) SEQUENCE DESCRIPTION: SEQ ID NO: 72:

Xaa     Xaa     Arg     Glu     Xaa     Xaa
                1                               5

( 2 ) INFORMATION FOR SEQ ID NO: 73 : 1 to 6:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 x 10 Array Sequence Ligand for
                  Streptavidin Test, Address 73.
            ( B ) LOCATION:
            ( C ) IDENTIFICATION METHOD: Constructed using an
                  Arris Pharmaceutical PILOT Support Array System
            ( D ) OTHER INFORMATION: Exhibits specific binding
                  activity with Streptavidin. Xaa represents a
                  random amino acid selected from mixtures of the
                  following 10 amino acids to give equal
                  incorporation: Nle, His, Pro, Gln, Tyr, Gly, Phe,
                  Arg, Glu, βAla. Where Leu or Ala is specified at
                  any position in the sequence, then Leu refers to
                  Nle (or normal-leucine) and Ala refers to βAla (or
                  beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 73: 1 to 6

( x i ) SEQUENCE DESCRIPTION: SEQ ID NO: 73:

Xaa    Xaa    Arg    Arg    Xaa    Xaa
        1                                                   5

( 2 ) INFORMATION FOR SEQ ID NO: 74:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
              Streptavidin Test, Addresses 074.
        ( B ) LOCATION:
        ( C ) IDENTIFICATION METHOD: Constructed using an
              Arris Pharmaceutical PILOT Support Array System
        ( D ) OTHER INFORMATION: Biological activity unknown.
              Xaa represents a random amino acid selected from
              mixtures of the following 10 amino acids to give
              equal incorporation: Nle, His, Pro, Gln, Tyr, Gly,
              Phe, Arg, Glu, βAla. Where Leu or Ala is
              specified at any position in the sequence, then Leu
              refers to Nle (or normal-leucine) and Ala refers to
              βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 74: 1 to 6

( x i ) SEQUENCE DESCRIPTION: SEQ ID NO: 74:

Xaa    Xaa    Arg    Phe    Xaa    Xaa
        1                                                   5

( 2 ) INFORMATION FOR SEQ ID NO: 75:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
              Streptavidin Test, Address 075.
        ( B ) LOCATION:
        ( C ) IDENTIFICATION METHOD: Constructed using an
              Arris Pharmaceutical PILOT Support Array System
        ( D ) OTHER INFORMATION: Biological activity unknown.
              Xaa represents a random amino acid selected from
              mixtures of the following 10 amino acids to give
              equal incorporation: Nle, His, Pro, Gln, Tyr, Gly,
              Phe, Arg, Glu, βAla. Where Leu or Ala is
              specified at any position in the sequence, then Leu
              refers to Nle (or normal-leucine) and Ala refers to
              βAla (or beta- alanine).

( x ) PUBLICATION INFORMATION:
        ( A ) AUTHORS:
        ( B ) TITLE:

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 75: 1 to 6

(xi) SEQUENCE DESCRIPTION: SEQ ID NO: 75:

Xaa   Xaa   Arg   Gly   Xaa   Xaa
 1                        5

(2) INFORMATION FOR SEQ ID NO: 76:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 076.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 76: 1 to 6

(xi) SEQUENCE DESCRIPTION: SEQ ID NO: 76:

Xaa   Xaa   Arg   Tyr   Xaa   Xaa
 1                        5

(2) INFORMATION FOR SEQ ID NO: 77:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 77.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 77: 1 to 6

( x i ) SEQUENCE DESCRIPTION: SEQ ID NO: 77:

```
Xaa    Xaa    Arg    Gln    Xaa    Xaa
1                          5
```

( 2 ) INFORMATION FOR SEQ ID NO: 78:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 78.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 78: 1 to 6

( x i ) SEQUENCE DESCRIPTION: SEQ ID NO: 78:

```
Xaa    Xaa    Arg    Pro    Xaa    Xaa
1                          5
```

( 2 ) INFORMATION FOR SEQ ID NO: 79:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide (A) DESCRIPTION:

(ix) FEATURE:
    (A) NAME/KEY: 10 x 10 Array Sequence Ligands for
        Streptavidin Test, Address 79.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 79: 1 to 6

(xi) SEQUENCE DESCRIPTION: SEQ ID NO: 79:

Xaa    Xaa    Arg    His    Xaa    Xaa
    1                                       5

(2) INFORMATION FOR SEQ ID NO: 80:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for
            Streptavidin Test, Address 80.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 80: 1 to 6

(xi) SEQUENCE DESCRIPTION: SEQ ID NO: 80:

Xaa    Xaa    Arg    Leu    Xaa    Xaa
    1                                       5

( 2 ) INFORMATION FOR SEQ ID NO: 81:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 081.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 81: 1 to 6

( x i ) SEQUENCE DESCRIPTION: SEQ ID NO: 81:

Xaa    Xaa    Glu    Ala    Xaa    Xaa
        1                                          5

( 2 ) INFORMATION FOR SEQ ID NO: 82:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 82.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

(H) DOCUMENT NUMBER:
(I) FILING DATE:
(J) PUBLICATION DATE:
(K) RELEVANT RESIDUES IN SEQ ID NO: 82: 1 to 6

(xi) SEQUENCE DESCRIPTION: SEQ ID NO: 82:

Xaa Xaa Glu Glu Xaa Xaa
1                     5

(2) INFORMATION FOR SEQ ID NO: 83:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 83.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 83: 1 to 6

(xi) SEQUENCE DESCRIPTION: SEQ ID NO:83:

Xaa Xaa Glu Arg Xaa Xaa
1                     5

(2) INFORMATION FOR SEQ ID NO: 84:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 84.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 84: 1 to 6

(xi) SEQUENCE DESCRIPTION: SEQ ID NO: 84:

Xaa    Xaa    Glu    Phe    Xaa    Xaa
    1                                            5

(2) INFORMATION FOR SEQ ID NO: 85:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for
            Streptavidin Test, Address 85.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 85: 1 to 6

(xi) SEQUENCE DESCRIPTION: SEQ ID NO: 85:

Xaa    Xaa    Glu    Gly    Xaa    Xaa
    1                                            5

(2) INFORMATION FOR SEQ ID NO: 86:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 x 10 Array Sequence Ligands for
            Streptavidin Test, Address 86.

(B) LOCATION:
(C) IDENTIFICATION METHOD: Constructed using an
    Arris Pharmaceutical PILOT Support Array System
(D) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, βAla. Where Leu or Ala is
    specified at any position in the sequence, then Leu
    refers to Nle (or normal-leucine) and Ala refers to
    βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 86: 1 to 6

(xi) SEQUENCE DESCRIPTION: SEQ ID NO: 86:

```
Xaa    Xaa    Glu    Tyr    Xaa    Xaa
1                           5
```

(2) INFORMATION FOR SEQ ID NO: 87:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 87.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 87: 1 to 6

(xi) SEQUENCE DESCRIPTION: SEQ ID NO: 87:

```
Xaa    Xaa    Glu    Gln    Xaa    Xaa
1                           5
```

(2) INFORMATION FOR SEQ ID NO: 88:

(i) SEQUENCE CHARACTERISTICS:
    (A) LENGTH: 6

(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for
Streptavidin Test, Address 88.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 88: 1 to 6

(xi) SEQUENCE DESCRIPTION: SEQ ID NO: 88:

Xaa   Xaa   Glu   Pro   Xaa   Xaa
1                       5

(2) INFORMATION FOR SEQ ID NO: 89:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for
Streptavidin Test, Address 089.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 89: 1 to 6

( x i ) SEQUENCE DESCRIPTION: SEQ ID NO: 89:

Xaa  Xaa  Glu  His  Xaa  Xaa
     1                    5

( 2 ) INFORMATION FOR SEQ ID NO: 90:

( i ) SEQUENCE CHARACTERISTICS:
   ( A ) LENGTH: 6
   ( B ) TYPE: Amino Acids
   ( C ) STRANDEDNESS:
   ( D ) TOPOLOGY: Linear ( i i ) MOLECULE TYPE: Peptide
   ( A ) DESCRIPTION:

( i x ) FEATURE:
   ( A ) NAME/KEY: 10 x 10 Array Sequence Ligands for
     Streptavidin Test, Address 90.
   ( B ) LOCATION:
   ( C ) IDENTIFICATION METHOD: Constructed using an
     Arris Pharmaceutical PILOT Support Array System
   ( D ) OTHER INFORMATION: Biological activity unknown.
     Xaa represents a random amino acid selected from
     mixtures of the following 10 amino acids to give
     equal incorporation: Nle, His, Pro, Gln, Tyr, Gly,
     Phe, Arg, Glu, βAla. Where Leu or Ala is
     specified at any position in the sequence, then Leu
     refers to Nle (or normal-leucine) and Ala refers to
     βAla (or beta- alanine).

( x ) PUBLICATION INFORMATION:
   ( A ) AUTHORS:
   ( B ) TITLE:
   ( C ) JOURNAL:
   ( D ) VOLUME:
   ( E ) ISSUE:
   ( F ) PAGES:
   ( G ) DATE:
   ( H ) DOCUMENT NUMBER:
   ( I ) FILING DATE:
   ( J ) PUBLICATION DATE:
   ( K ) RELEVANT RESIDUES IN SEQ ID NO: 90: 1 to 6

( x i ) SEQUENCE DESCRIPTION: SEQ ID NO: 90:

Xaa  Xaa  Glu  Leu  Xaa  Xaa
     1                    5

( 2 ) INFORMATION FOR SEQ ID NO: 91:

( i ) SEQUENCE CHARACTERISTICS:
   ( A ) LENGTH: 6
   ( B ) TYPE: Amino Acids
   ( C ) STRANDEDNESS:
   ( D ) TOPOLOGY: Linear ( i i ) MOLECULE TYPE: Peptide
   ( A ) DESCRIPTION:

( i x ) FEATURE:
   ( A ) NAME/KEY: 10 x 10 Array Sequence Ligands for
     Streptavidin Test, Address 091.
   ( B ) LOCATION:
   ( C ) IDENTIFICATION METHOD: Constructed using an
     Arris Pharmaceutical PILOT Support Array System
   ( D ) OTHER INFORMATION: Biological activity unknown.
     Xaa represents a random amino acid selected from
     mixtures of the following 10 amino acids to give
     equal incorporation: Nle, His, Pro, Gln, Tyr, Gly,
     Phe, Arg, Glu, βAla. Where Leu or Ala is
     specified at any position in the sequence, then Leu
     refers to Nle (or normal-leucine) and Ala refers to
     βAla (or beta- alanine).

( x ) PUBLICATION INFORMATION:
   ( A ) AUTHORS:
   ( B ) TITLE:

( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 91: 1 to 6

( x i ) SEQUENCE DESCRIPTION: SEQ ID NO: 91:

```
Xaa   Xaa   Ala   Ala   Xaa   Xaa
 1                        5
```

( 2 ) INFORMATION FOR SEQ ID NO: 92:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 x 10 Array Sequence Ligands for Streptavidin Test, Address 092.
    ( B ) LOCATION:
    ( C ) IDENTIFICATION METHOD: Constructed using an Arris Pharmaceutical PILOT Support Array System
    ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, βAla. Where Leu or Ala is specified at any position in the sequence, then Leu refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 92: 1 to 6

( x i ) SEQUENCE DESCRIPTION: SEQ ID NO: 92:

```
Xaa   Xaa   Ala   Glu   Xaa   Xaa
 1                        5
```

( 2 ) INFORMATION FOR SEQ ID NO: 93:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 x 10 Array Sequence Ligands for Streptavidin Test, Address 93.
    ( B ) LOCATION:
    ( C ) IDENTIFICATION METHOD: Constructed using an Arris Pharmaceutical PILOT Support Array System
    ( D ) OTHER INFORMATION: Biological activity unknown. Xaa represents a random amino acid selected from mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 93: 1 to 6

( x i ) SEQUENCE DESCRIPTION: SEQ ID NO: 93:

Xaa    Xaa    Ala    Arg    Xaa    Xaa
    1                                        5

( 2 ) INFORMATION FOR SEQ ID NO: 94:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 94.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 94: 1 to 6

( x i ) SEQUENCE DESCRIPTION: SEQ ID NO: 94:

Xaa    Xaa    Ala    Phe    Xaa    Xaa
        1                                        5

( 2 ) INFORMATION FOR SEQ ID NO: 95:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide (A) DESCRIPTION:

(ix) FEATURE:
(A) NAME/KEY: 10 x 10 Array Sequence Ligands for
Streptavidin Test, Address 95.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 95: 1 to 6

(xi) SEQUENCE DESCRIPTION: SEQ ID NO: 95:

```
Xaa    Xaa    Ala    Gly    Xaa    Xaa
1                          5
```

(2) INFORMATION FOR SEQ ID NO: 96:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 x 10 Array Sequence Ligands for
Streptavidin Test, Address 96.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, βAla. Where Leu or Ala is
specified at any position in the sequence, then Leu
refers to Nle (or normal-leucine) and Ala refers to
βAla (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 96: 1 to 6

(xi) SEQUENCE DESCRIPTION: SEQ ID NO: 96:

```
Xaa    Xaa    Ala    Tyr    Xaa    Xaa
1                          5
```

( 2 ) INFORMATION FOR SEQ ID NO: 97:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 97.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 97: 1 to 6

( x i ) SEQUENCE DESCRIPTION: SEQ ID NO: 97:

Xaa    Xaa    Ala    Gln    Xaa    Xaa
        1                                            5

( 2 ) INFORMATION FOR SEQ ID NO: 98:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 x 10 Array Sequence Ligands for
            Streptavidin Test, Address 98.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, βAla. Where Leu or Ala is
            specified at any position in the sequence, then Leu
            refers to Nle (or normal-leucine) and Ala refers to
            βAla (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

(H) DOCUMENT NUMBER:
(I) FILING DATE:
(J) PUBLICATION DATE:
(K) RELEVANT RESIDUES IN SEQ ID NO: 98: 1 to 6

(xi) SEQUENCE DESCRIPTION: SEQ ID NO: 98:

Xaa Xaa Ala Pro Xaa Xaa
1              5

(2) INFORMATION FOR SEQ ID NO: 99:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 99.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to
        βAla (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 99: 1 to 6

(xi) SEQUENCE DESCRIPTION: SEQ ID NO: 99:

Xaa Xaa Ala His Xaa Xaa
1              5

(2) INFORMATION FOR SEQ ID NO: 100:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 x 10 Array Sequence Ligands for
        Streptavidin Test, Address 100.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, βAla. Where Leu or Ala is
        specified at any position in the sequence, then Leu
        refers to Nle (or normal-leucine) and Ala refers to βAla (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 100: 1 to 6

( x i ) SEQUENCE DESCRIPTION: SEQ ID NO: 100:

```
Xaa   Xaa   Ala   Leu   Xaa   Xaa
 1                        5
```

( 2 ) INFORMATION FOR SEQ ID NO: 101:

( i ) SEQUENCE CHARACTERISTICS:
        ( A ) LENGTH: 8
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: Pepsyn-K Bead Test Peptide
        ( B ) LOCATION:
        ( C ) IDENTIFICATION METHOD: Constructed using a
            Milligen/Biosearch Model 9600 peptide synthesizer.
        ( D ) OTHER INFORMATION: Biological activity not determined.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 101: From 1 to 8

( x i ) SEQUENCE DESCRIPTION: SEQ ID NO: 101:

```
Ala   Ala   Ala   Leu   Ala   Leu   Ala   Ala
 1                        5
```

( 2 ) INFORMATION FOR SEQ ID NO: 102:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: Streptavidin test VYGFRQ peptide
        ( B ) LOCATION:
        ( C ) IDENTIFICATION METHOD: Constructed using a
            Millipore Model 9600 peptide synthesizer
        ( D ) OTHER INFORMATION: Binds to labeled streptavidin.
            Best synthesized hexapeptide combination for
            binding to streptavidin biotin-binding protein;
            biological activity not determined.

( x i ) SEQUENCE DESCRIPTION: SEQ ID NO: 102:

```
        Val    Tyr    Gly    Phe    Arg    Gln
        1                           5
```

( 2 ) INFORMATION FOR SEQ ID NO: 103:

( i ) SEQUENCE CHARACTERISTICS:
        ( A ) LENGTH: 9
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: Streptavidin binding nona-peptide
        ( B ) LOCATION:
        ( C ) IDENTIFICATION METHOD: Constructed using a
            Millipore (Milligen/Biosearch) Model 9600 peptide
            synthesizer
        ( D ) OTHER INFORMATION: Combination nona-peptide of the
            first three amino acid sequence of the HPQVYGFRQ hexa-
            peptide sequence HPQVFV and the hexa-peptide sequence
            VYGFRQ. Exhibits strong binding with labeled
            streptavidin; biological activity not determined.

( x i ) SEQUENCE DESCRIPTION: SEQ ID NO: 103:

```
        His    Pro    Gln    Val    Tyr    Gly    Phe    Arg    Gln
        1                           5
```

We claim:

1. A biological screening assembly comprising in operative combination:

a) a one piece, inert substrate carrier plate having an array of discrete, individually addressable areas for receiving a substrate material, said substrate material chemically functionalized for assembly of biopolymers thereon;

b) a substrate material selected from the group consisting of:

i) an acid chloride activated surface;

ii) a particulate material;

iii) a functionalized polyolefin disc; and iv) a functionalized porous polyolefin disc; wherein said substrate material in at least some of said discrete, individually addressable areas is coated with a hydrophilic polar multifunctionalized polysaccharide chain covalently coupled to said substrate material; wherein said hydrophilic polar multi-functionalized polysaccharide chain is covalently coupled at multiple points to said substrate material spaced along the length of each polysaccharide chain, wherein said covalent bonds are present in an amount sufficient to minimize loss of said polysaccharide chain from said support upon exposure to trifluoroacetic acid and to minimize the effect of hydrolysis in said polysaccharide chain during peptide synthesis deprotection, to form a thin film three dimensional functionalized matrix layer above said substrate in an open, freely permeable configuration for the covalent tethering of ligands thereon, and for access thereinto of target molecules for affinity binding to said ligands which are tetherable to said thin film three dimensional functionalized matrix by covalent bonds for affinity screening of target molecules, in which at least one of said substrate material is secured to each of said discrete, individually addressable areas; and each of said substrate material is wholly contained within the boundary of each discrete individually addressable area.

2. The biopolymer screening assembly of claim 1 wherein said plate is a polyolefin, and said polysaccharide chain has a low molar percentage of crosslinking.

3. The biopolymer screening assembly of claim 1 wherein said particulate material is selected from at least one member of the group consisting of polydimethylacrylamide particles, silica beads, and MBHA polystyrene beads.

4. The biopolymer screening assembly of claim 3 wherein said polydimethylacrylamide particles are Kieselguhr-encapsulated beads physically bonded to said plate in said discrete, individually addressable areas.

5. The biopolymer screening assembly of claim 1 wherein said substrate material in at least some of the discrete, individually addressable areas is functionalized with at least one spacer arm.

6. The biopolymer screening assembly of claim 5 wherein said spacer arm is amino functionalized.

7. A biological screening system comprising in operative combination:

a) an inert support plate having an array of a plurality of discrete, individually addressable areas for receiving a substrate material;

b) substrate material chemically functionalized for assembly of biopolymers thereon secured to each of said addressable areas in which said substrate material is wholly contained within the boundary of each discrete, individually addressable area;

c) an elastomeric barrier gasket sheet overlying said inert support plate having an array of holes therethrough aligned with said array of discrete, individually addressable areas for access to said substrate material, said holes independent and isolated from one another; and d) an apertured block disposed on said elastomeric barrier gasket, said apertured block having a plurality of slots passing therethrough, each of said slots oriented to provide a common well for simultaneous access of reagents and biomonomer solutions for the synthesis of biopolymers to a plurality of said substrate materials in said array.

8. The biopolymer screening system of claim 7 wherein said array of a plurality of discrete, individually addressable areas is substantially rectilinear; said plurality of slots are substantially linear; and said apertured block is orientable on said array in at least two rotationally different positions with respect to each other to permit synthesis of biopolymers of defined sequences from chemical components placed in said wells.

9. The biopolymer screening system of claim 8 wherein said array of a plurality of discrete, individually addressable areas is selected from a rectangular 10×10, 20×20, 50×50, 100×100, 200×200 or 400×400 array; and said apertured block is selected from a corresponding block having 10, 20, 50, 100, 200 or 400 linear slots positioned to provide access to all the substrate areas of said plate.

10. The biopolymer screening system of claim 7 wherein said array of a plurality of discrete, individually addressable areas is radial; and said apertured block includes a plurality of coordinate concentric semi-circular slots.

11. The biopolymer screening system of claim 7 wherein said apertured block includes means for uniquely identifying each of said slots.

12. The biopolymer screening system of claim 11 wherein said apertured block includes means for identifying the orientation of said slots to said array of a plurality of discrete, individually addressable areas to provide accurate orientation upon each rotation.

13. The biopolymer screening system of claim 12 wherein said inert support plate includes means for uniquely identifying each of said plurality of discrete, individually addressable areas of said array.

14. The biopolymer screening system of claim 9 wherein said apertured block includes means for uniquely identifying each of said slots and means for identifying the orientation of said slots to said array of a plurality of discrete, individually addressable areas to provide accurate orientation upon each rotation; and said inert support plate includes means for uniquely identifying each of said plurality of discrete, individually addressable areas areas of said array.

15. The biopolymer screening system of claim 10 wherein said apertured block includes means for uniquely identifying each of said slots and means for identifying the orientation of said slots to said array of a plurality of discrete, individually addressable areas to provide accurate orientation upon each rotation; and said inert support plate includes means for uniquely identifying each of said plurality of discrete, individually addressable areas areas of said array.

16. The biopolymer screening system of claim 7 wherein at least some of the substrate material secured to each of the discrete, individually addressable areas comprise porous polyolefin-discs removably received in holes in said plate, wherein said substrate material is coated with a hydrophilic polar multi-functionalized polymer film.

17. A biological screening assembly comprising in operative combination:

a) a one piece, inert support plate having an integral array of a plurality of discrete, individually addressable areas for receiving a biopolymer-retaining substrate material said plurality of discrete, individually addressable areas having a least one drain hole therein passing through said support plate and said holes being of sufficiently small diameter so as to permit retention of said substrate material in said areas; and b) biopolymer-retaining substrate material which is secured to each of said plurality of discrete, individually addressable areas, said substrate material wholly contained within the boundary of each discrete individually addressable area; wherein at least some of the substrate material secured to each of the discrete, individually addressable areas comprise porous polyolefin-discs removably received in holes of plate, and said substrate material is coated with a hydrophilic polar multifunctionalized polymer film;

d) a border block overlying said support plate said border block providing a leakproof barrier at the perimeter of said inert support plate to allow the simultaneous exposure of all reaction sites to a common reagent bath solution;

e) a vacuum base underlying said plate;

f) means to seal said plate between said border block and said vacuum base to permit withdrawal of the solution applied on the entirety of said plate through said porous disc and said holes.

* * * * *